(12) United States Patent
Laugharn, Jr. et al.

(10) Patent No.: US 8,353,619 B2
(45) Date of Patent: Jan. 15, 2013

(54) METHODS AND APPARATUS FOR TREATING SAMPLES WITH ACOUSTIC ENERGY

(75) Inventors: James A. Laugharn, Jr., Winchester, MA (US); Brevard S. Garrison, Reading, MA (US); Douglas A. Yates, North Andover, MA (US)

(73) Assignee: Covaris, Inc., Woburn, MA (US)

( * ) Notice: Subject to any disclaimer, the term of this patent is extended or adjusted under 35 U.S.C. 154(b) by 937 days.

(21) Appl. No.: 11/888,708

(22) Filed: Aug. 1, 2007

(65) Prior Publication Data

US 2008/0031094 A1    Feb. 7, 2008

Related U.S. Application Data

(60) Provisional application No. 60/834,979, filed on Aug. 1, 2006, provisional application No. 60/923,335, filed on Apr. 13, 2007.

(51) Int. Cl.
*B01F 11/00*    (2006.01)
(52) U.S. Cl. .................................. 366/127; 366/108
(58) Field of Classification Search .................. 366/108, 366/110, 127; 422/127, 128
See application file for complete search history.

(56) References Cited

U.S. PATENT DOCUMENTS

| | | | |
|---|---|---|---|
| 1,734,975 A | | 11/1929 | Loomis et al. |
| 2,424,375 A | * | 7/1947 | Van Allen .................. 116/137 A |
| 2,447,061 A | | 8/1948 | Franklin |
| 2,565,159 A | | 8/1951 | Williams |
| 2,578,505 A | | 12/1951 | Carlin |
| 2,585,103 A | | 2/1952 | Fitzgerald |
| 2,632,634 A | | 3/1953 | Williams |
| 2,738,172 A | | 3/1956 | Spiess, Jr. et al. |
| 2,855,526 A | | 10/1958 | Jones |
| 2,864,592 A | | 12/1958 | Camp |
| 2,916,265 A | | 12/1959 | Towne |
| 2,950,725 A | | 8/1960 | Jacke et al. |
| 3,066,686 A | | 12/1962 | O'Neill |
| 3,194,640 A | | 7/1965 | Nesh |
| 3,292,910 A | | 12/1966 | Martner |
| 3,352,311 A | * | 11/1967 | Murphy .......................... 134/86 |
| 3,396,286 A | | 8/1968 | Anderson et al. |
| 3,481,186 A | | 12/1969 | Plofsk et al. |
| 3,503,805 A | * | 3/1970 | Denyes ............................ 134/1 |
| 3,596,883 A | * | 8/1971 | Brech ........................... 366/115 |

(Continued)

FOREIGN PATENT DOCUMENTS

DE    2557668    6/1977

(Continued)

OTHER PUBLICATIONS

Notice of Allowance from related U.S. Appl. No. 11/006,002.

(Continued)

*Primary Examiner* — David Sorkin
(74) *Attorney, Agent, or Firm* — Wolf, Greenfield & Sacks, P.C.

(57) ABSTRACT

This invention relates to systems and methods for applying acoustic energy to a sample. According to one aspect of the invention, a system comprises a housing, a chamber for receiving the sample, an acoustic energy source for providing a focused acoustic field to the sample according to a treatment protocol, a processor for determining the treatment protocol, a sensor for detecting information about the sample, and a user interface for communicating with a user.

34 Claims, 10 Drawing Sheets

U.S. PATENT DOCUMENTS

| | | | | |
|---|---|---|---|---|
| 3,604,270 | A | 9/1971 | Falk | |
| 3,614,069 | A | 10/1971 | Murry | |
| 3,743,523 | A | 7/1973 | Bodine | |
| 3,807,704 | A | 4/1974 | Janzen et al. | |
| 3,837,805 | A | 9/1974 | Boucher | |
| 3,851,861 | A * | 12/1974 | Cummins et al. | 366/114 |
| 3,876,980 | A | 4/1975 | Haemmig et al. | |
| 3,919,558 | A | 11/1975 | Brouillette et al. | |
| 3,972,614 | A * | 8/1976 | Johansen et al. | 356/36 |
| 4,028,933 | A | 6/1977 | Lemons et al. | |
| 4,193,818 | A * | 3/1980 | Young et al. | 134/1 |
| 4,307,964 | A | 12/1981 | Dudgeon et al. | |
| RE31,779 | E | 12/1984 | Alliger | |
| 4,488,816 | A | 12/1984 | Vota et al. | |
| 4,541,281 | A | 9/1985 | Chubachi et al. | |
| 4,571,087 | A | 2/1986 | Ranney | |
| 4,644,808 | A | 2/1987 | Lecoffre | |
| 4,764,905 | A | 8/1988 | Granz et al. | |
| 4,834,124 | A | 5/1989 | Honda et al. | |
| 4,862,060 | A | 8/1989 | Scott et al. | |
| 4,870,982 | A * | 10/1989 | Liu | 134/135 |
| 4,879,011 | A | 11/1989 | Schram | |
| 4,889,122 | A | 12/1989 | Watmough et al. | |
| 4,926,871 | A | 5/1990 | Ganguly et al. | |
| 4,930,532 | A * | 6/1990 | Mayer | 134/184 |
| 4,983,189 | A | 1/1991 | Peterson et al. | |
| 5,026,167 | A | 6/1991 | Berliner, III | |
| 5,037,481 | A | 8/1991 | Bran | |
| 5,086,810 | A * | 2/1992 | Carroll | 139/1 C |
| 5,178,173 | A * | 1/1993 | Erickson et al. | 134/184 |
| 5,368,054 | A | 11/1994 | Koretsky et al. | |
| 5,395,592 | A | 3/1995 | Bolleman et al. | |
| 5,409,594 | A | 4/1995 | Al-Jiboory et al. | |
| 5,484,573 | A | 1/1996 | Berger et al. | |
| 5,523,058 | A | 6/1996 | Umemura et al. | |
| 5,601,526 | A | 2/1997 | Chapelon et al. | |
| 5,623,095 | A | 4/1997 | Beller | |
| 5,631,425 | A | 5/1997 | Wang et al. | |
| 5,639,423 | A | 6/1997 | Northrup et al. | |
| 5,681,396 | A | 10/1997 | Madanshetty | |
| 5,688,406 | A | 11/1997 | Dickinson et al. | |
| 5,711,327 | A * | 1/1998 | Fields | 134/105 |
| 5,736,100 | A | 4/1998 | Miyake et al. | |
| 5,759,162 | A | 6/1998 | Oppelt et al. | |
| 5,779,985 | A | 7/1998 | Sucholeiki | |
| 5,803,099 | A | 9/1998 | Sakuta et al. | |
| 5,831,166 | A | 11/1998 | Kozuka et al. | |
| 5,834,648 | A | 11/1998 | Wang et al. | |
| 5,876,671 | A * | 3/1999 | Beugelsdijk et al. | 422/67 |
| 5,890,802 | A | 4/1999 | Evensen et al. | |
| 5,962,338 | A | 10/1999 | Sucholeiki | |
| 5,993,671 | A | 11/1999 | Peltzer | |
| 6,003,388 | A | 12/1999 | Oeftering | |
| 6,010,316 | A | 1/2000 | Haller et al. | |
| 6,039,309 | A | 3/2000 | Kuklinski | |
| 6,042,556 | A | 3/2000 | Beach et al. | |
| 6,086,821 | A | 7/2000 | Lee | |
| 6,100,084 | A | 8/2000 | Miles et al. | |
| 6,210,128 | B1 | 4/2001 | Rife et al. | |
| 6,224,778 | B1 | 5/2001 | Peltzer | |
| 6,244,738 | B1 | 6/2001 | Yasuda et al. | |
| 6,277,332 | B1 | 8/2001 | Sucholeiki | |
| 6,284,113 | B1 | 9/2001 | Bjornson et al. | |
| 6,291,180 | B1 | 9/2001 | Chu | |
| 6,361,747 | B1 | 3/2002 | Dion et al. | |
| 6,413,783 | B1 | 7/2002 | Wohlstadter et al. | |
| 6,440,725 | B1 | 8/2002 | Pourahmadi et al. | |
| 6,515,030 | B1 | 2/2003 | Bechtel et al. | |
| 6,534,018 | B1 * | 3/2003 | Baker et al. | 422/128 |
| 6,699,711 | B1 | 3/2004 | Hahn et al. | |
| 6,719,449 | B1 | 4/2004 | Laugharn, Jr. et al. | |
| 6,737,021 | B2 | 5/2004 | Watari et al. | |
| 6,855,277 | B2 * | 2/2005 | Baker et al. | 264/4.3 |
| 6,855,296 | B1 * | 2/2005 | Baker et al. | 422/130 |
| 6,948,843 | B2 | 9/2005 | Laugharn, Jr. et al. | |
| 7,211,927 | B2 | 5/2007 | Puskas | |
| 7,329,039 | B2 | 2/2008 | Laugharn, Jr. et al. | |
| 7,481,918 | B2 * | 1/2009 | Morrison et al. | 210/96.1 |
| 7,491,527 | B2 * | 2/2009 | Yuan et al. | 435/306.1 |
| 7,521,023 | B2 * | 4/2009 | Laugharn et al. | 422/128 |
| 2002/0009015 | A1 * | 1/2002 | Laugharn et al. | 366/108 |
| 2003/0124033 | A1 * | 7/2003 | Baker et al. | 422/128 |
| 2003/0165482 | A1 | 9/2003 | Rolland et al. | |
| 2004/0054286 | A1 | 3/2004 | Audain et al. | |
| 2004/0076545 | A1 | 4/2004 | Watari et al. | |
| 2004/0264293 | A1 | 12/2004 | Laugharn et al. | |
| 2005/0142664 | A1 | 6/2005 | Loney | |
| 2005/0150830 | A1 | 7/2005 | Laugharn et al. | |
| 2005/0235740 | A1 | 10/2005 | Desie et al. | |
| 2006/0029525 | A1 | 2/2006 | Laugharn et al. | |
| 2006/0158956 | A1 | 7/2006 | Laugharn et al. | |
| 2007/0053795 | A1 | 3/2007 | Laugharn et al. | |
| 2008/0031094 | A1 | 2/2008 | Laugharn et al. | |
| 2008/0050289 | A1 | 2/2008 | Laugharn et al. | |
| 2008/0056960 | A1 | 3/2008 | Laugharn et al. | |
| 2008/0226495 | A1 * | 9/2008 | Sparks | 422/20 |
| 2008/0233001 | A1 * | 9/2008 | Ricciardi et al. | 422/20 |
| 2009/0000639 | A1 * | 1/2009 | Tribelsky et al. | 134/1 |
| 2009/0095685 | A1 * | 4/2009 | Morrison et al. | 210/695 |
| 2009/0211615 | A1 * | 8/2009 | Ho | 134/56 R |

FOREIGN PATENT DOCUMENTS

| | | |
|---|---|---|
| DE | 19534955 | 3/1996 |
| DE | 19617924 | 11/1997 |
| DE | 19756874 | 6/1999 |
| DE | 19820466 | 11/1999 |
| DE | 10325307 | 7/2004 |
| EP | 0643982 | 3/1995 |
| EP | 0709136 A1 | 1/1996 |
| EP | 0707892 A1 | 4/1996 |
| EP | 1128185 | 8/2001 |
| EP | 1344562 | 9/2003 |
| GB | 1015962 | 1/1966 |
| GB | 1105962 | 3/1968 |
| GB | 1536693 | 12/1978 |
| WO | WO 9502456 | 1/1995 |
| WO | WO-9858417 | 12/1998 |
| WO | WO-0025125 | 5/2000 |
| WO | WO-2006033307 | 3/2006 |
| WO | WO-2007016605 | 2/2007 |

OTHER PUBLICATIONS

"Early experience with high-intensity focused ultrasound for the treatment of benign prostatic hypertrophy", Sullivan et al, British Journal of Uriology, vol. 79 pp. 172-176, dated 1997.

"A prototype of a 500kHz ultrasonic Matricidal Device: Beam Scanner, Application to in-vivo heel bone quantitative characterization", Defontaine et al, 1999 IEEE Ultrasonics Symposium, pp. 1585-1588, dated 1999.

"A new method for the generation and use of focused ultrasound in experimental biology", as submitted on Jul. 6, 1942, Lynn et al., The Journal of General Physiology, vol. 26, The Rockefeller University Press, pp. 179-193, copyright 1942.

"Some applications of Ultrasonics", Brockelsby, J. Sci. Instrum., vol. 40, pp. 153-156, dated 1963.

Steven V. Ley and Caroline M. R. Low, Ultrasound in Synthesis, Springer-Verlag 1989, pp. 18-28.

European Search Report and Office Action from European Application No. EP 07 02 2472 dated Jan. 15, 2009.

International Search Report and Written Opinion from International Patent Application PCT/US2004/040133 dated Apr. 20, 2005.

* cited by examiner

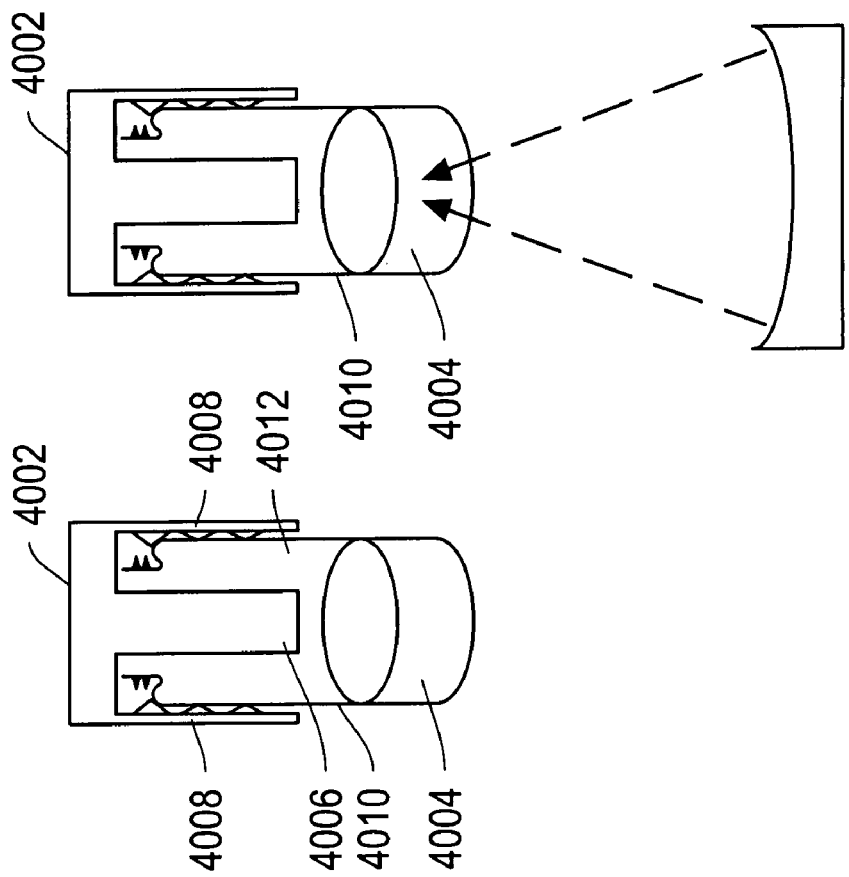
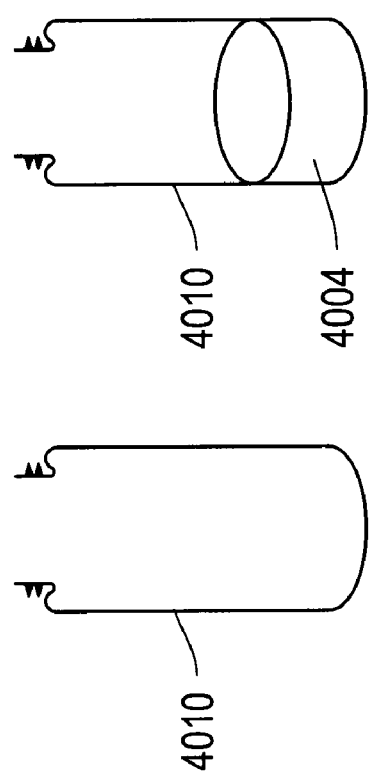
Figure 4A
Figure 4B
Figure 4C
Figure 4D

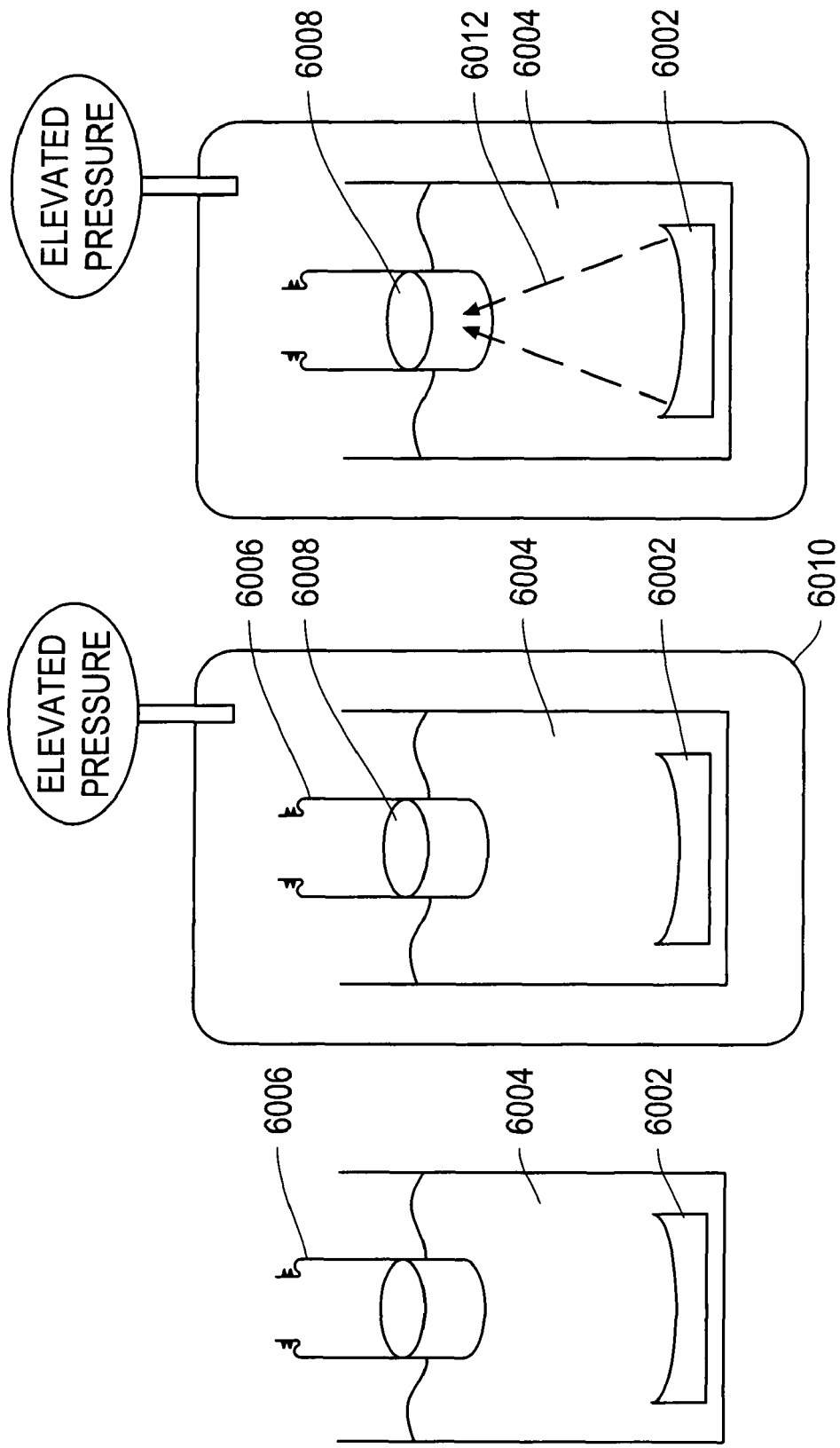

METHODS AND APPARATUS FOR TREATING SAMPLES WITH ACOUSTIC ENERGY

CROSS-REFERENCE TO RELATED APPLICATIONS

This application claims the benefit of U.S. Provisional Patent Application No. 60/834,979 filed Aug. 1, 2006 and entitled "Methods and Apparatus for Treating Samples with Acoustic Energy" and U.S. Provisional Patent Application No. 60/923,335 filed Apr. 13, 2007 and entitled "Methods and Apparatus for Focused Ultrasonic Sample Processing under High Pressure." The disclosure of each of the foregoing applications is incorporated herein by reference.

FIELD OF THE INVENTION

The invention generally relates to the field of controlled acoustic energy-emitting devices for treating biological and/or chemical material, and more particularly to performing Such treatment in a laboratory or benchtop setting.

BACKGROUND

Ultrasonics have been utilized for many years in a variety of diagnostic, therapeutic, and research purposes. Some uses of ultrasonic or acoustic energy in materials processing include breaking up and/or mixing of fluid suspensions of materials. Additional uses are in solubilizing or otherwise ensuring that all or substantially all of the constituents of a sample are in solution and/or in suspension. Regardless of the particular use, sample materials are typically contained in a plastic or glass enclosure, such as vials, tubes, culture plates/well, or micro-titer plates, with an acoustic transducer coupled to the sample by way of a coupling medium, such as water. Typically, systems in which acoustic energy is precisely controlled and transferred to a sample in a vessel are relatively low power. Examples of low power systems include high-frequency, low-intensity focused acoustic dispensing systems, which transfer droplets of sample from a fluid-air interface through an air gap to a receiving vessel, and high-frequency focused interrogation systems commonly used in non-destructive testing of materials. Alternatively, acoustic transducers can be directly immersed in the material to be treated. This type of system, in which an acoustic transducer directly contacts the sample, is capable of relatively high power; however, it is typically of lower frequency. A distinct disadvantage of lower frequency systems is the lack of control inherent with long wavelength acoustics. For example, the low-frequency probe-type sonicator typically used in biological and chemical laboratories is operated at approximately 15 KHz, which results in wavelengths in aqueous media measuring several centimeters. Other systems can implement both high-power and high-control processing of diverse samples. However, there exists a need for a system with both high-power and high-control which is easy to use on a routine basis with minimal a priori sample preparation, process optimization, or operator training.

The foregoing arrangements have been used for a number of applications, including large-scale batch processing, yet there is still a need for acoustic systems and methods that are more flexible, convenient, and effective, in particular for on-demand uses, such as for automated processing of small quantities of samples, for example, in laboratory or benchtop settings.

SUMMARY

The invention provides methods and systems for selectively exposing a sample or samples to acoustic energy in a benchtop or laboratory setting for the purpose of, for example, heating, fluidizing, mixing, stirring, disrupting, comminuting, sterilizing, or solubilizing the sample, or for enhancing a reaction in the sample. The foregoing applications are merely illustrative, and one skilled in the art will recognize other uses for the application of focused acoustic energy. Altering the sample in a controlled manner, especially biological and chemical samples, allows manipulation of the sample while preserving the viability, chemical and/or biological activity of the material. Samples may comprise one or more constituents such as, for example, solvents, reagents, nucleic acids, proteins, small organic or inorganic molecules, chemical compounds, or pharmaceutical or biopharmaceutical agents. Non-clinical samples may also advantageously be treated by acoustic energy. A sample to be processed with acoustic energy may be physically isolated in a vessel from the surrounding environment and an acoustic energy source (e.g., transducer) which applies acoustic energy to the sample. The acoustic energy may be applied to the sample through a coupling medium such as water.

The term "acoustic energy" used herein refers to acoustic energy, acoustic waves, acoustic pulses, including forms of ultrasonic energy and/or shock waves. As used herein, sonic energy/acoustic energy refers to the focused, high frequency (e.g., typically 100 kHz-100 MHz; greater than 500 kHz; greater than or approximately equal to 1 MHz; etc), short wavelength (e.g., approximately 1-1.5 mm), acoustic energy. As used herein, focal zone or focal point means an area where sonic energy converges and/or impinges on a target, although that area of convergence is not necessarily a single focused point. According to one aspect, the present invention provides an acoustic energy source that provides a focused acoustic field. The acoustic energy source can be a focused transducer having a focal length, which generates an ellipsoidal focal zone. The focused transducer may be spherical, ellipsoidal, cylindrical, or any other suitable shape. The acoustic focal length of the focused transducer may be any suitable length, e.g., from 0.1-65 mm or more in diameter. The focal zone resulting from the focused transducer may be between 0.1 millimeter and 2 centimeters in diameter, e.g., between 0.1 mm and 100 mm, or between 0.1 mm and 10 mm, and the axial length of the focal zone may be between 0.1 millimeter and 6 centimeters, for example, depending on the size of the sample vessel.

In one aspect, the present invention provides a benchtop apparatus that can treat a sample effectively with little input from a user. In certain embodiments, the apparatus may also offer the user varying degrees of control over the treatment applied to the sample. In certain embodiments, an apparatus of the invention may feature one or more components such as a user interface for communicating with the user or an easily accessed chamber for holding the sample.

In certain embodiments, an apparatus of the invention may include an interchangeable memory component for storing treatment protocols. Interchangeable memory components can include memory cards, flash drives, CDs, DVDs, CD-ROMs, diskettes, chips, and any other suitable memory storage device. Treatment protocols may be preprogrammed, adjust to inputs from the user, adjust to measured changes in the sample during the treatment process, be based on initial conditions or characteristics of the sample, and/or be configured manually by the user. Operation of the apparatus can be at least partially automated. Steps that may be automated include selecting treatment parameters, selecting a treatment protocol, initiating acoustic treatment, and monitoring of sample parameters during treatment.

For example, the acoustic energy delivered to the sample may be adjusted by the controller according to the volume of the sample, the sample temperature, and/or based on the type or concentration of particulate matter in the sample, for the purpose of, for example, comminuting the particles. The sensors may include temperature sensors, pressure sensors, optical sensors, such as infrared sensor, microscopes and/or video cameras, lasers, acoustic sensors such as electromagnetic or piezoelectric sensors, or a combination of such sensors. The sensors may be arranged coaxially or at an angle to each other.

The sensors may be employed for measuring a physical characteristic of one or more samples before, during and/or following acoustic treatment of the samples. The results of the measured characteristic can be stored for use in subsequent processing steps or to compile a treatment history for the sample(s). For example, samples may be selected for further processing or interchanged for other samples based on their previously measured characteristics, or samples may be grouped and/or classified based on treatment history. Similarly, a characteristic measured post-treatment can be assessed by itself or can be compared to the characteristic measured pre-treatment and used to determine whether a desired condition of the sample has been reached and/or to assign a subsequent treatment or processing step for the sample.

The samples may be coupled to the acoustic energy source by a liquid, semi-solid or solid medium. For example, the acoustic transducer may be placed in a tray surrounded by a fluid with a high transmissivity for the acoustic energy, and the semi-solid or solid layer may be placed between the fluid and the sample to prevent direct contact between the sample and the fluid. The semi-solid or solid layer may be made of silicone gel, elastomeric polyurethane, thermoplastic elastomer and the like, and may also have an additional cover layer to further protect the sample from contamination.

According to the systems and methods disclosed herein, pressure may be applied to the sample or to the medium transmitting the acoustic energy, for example, by pressurizing the fluid, to improve acoustic coupling between the acoustic energy source and the sample. In another embodiment, the isolated sample inside a vessel may be pressurized relative to standard atmospheric pressure (e.g., to 2, 3, 4, or more atmospheres of pressure) to improve sample processing. When focused acoustic energy is subsequently applied to the sample, the desired result may be obtained in a shorter time period and/or, in some applications, may also result in improved sample processing and output quality (e.g., a narrower size distribution in a sheared DNA strand population).

BRIEF DESCRIPTION OF THE DRAWINGS

Features and advantages of the invention will be apparent upon consideration of the following detailed description, taken in conjunction with the accompanying drawings, in which like reference characters refer to like parts and in which:

FIGS. 4A-4D depict an illustrative process for treating a pressurized sample with acoustic energy according to an embodiment of the invention;

FIGS. 6A-6C depict an illustrative process for treating a pressurized sample with acoustic energy according to an embodiment of the invention;

DESCRIPTION OF ILLUSTRATIVE
EMBODIMENTS AND EXAMPLES

Figure 1B:
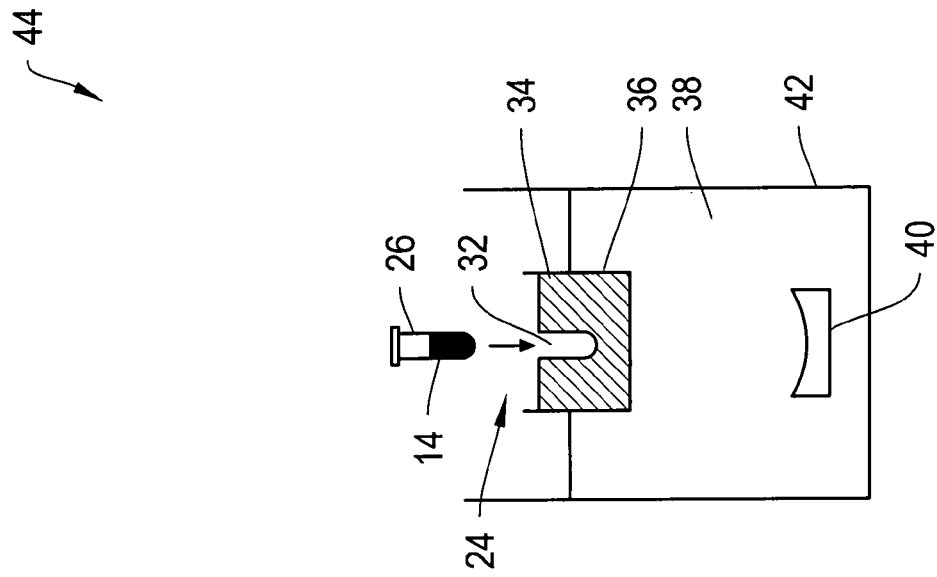
FIG. 1B depicts a cross-sectional view of the interior of a benchtop apparatus for processing a single sample according to an embodiment of the invention.
Figure 1A:
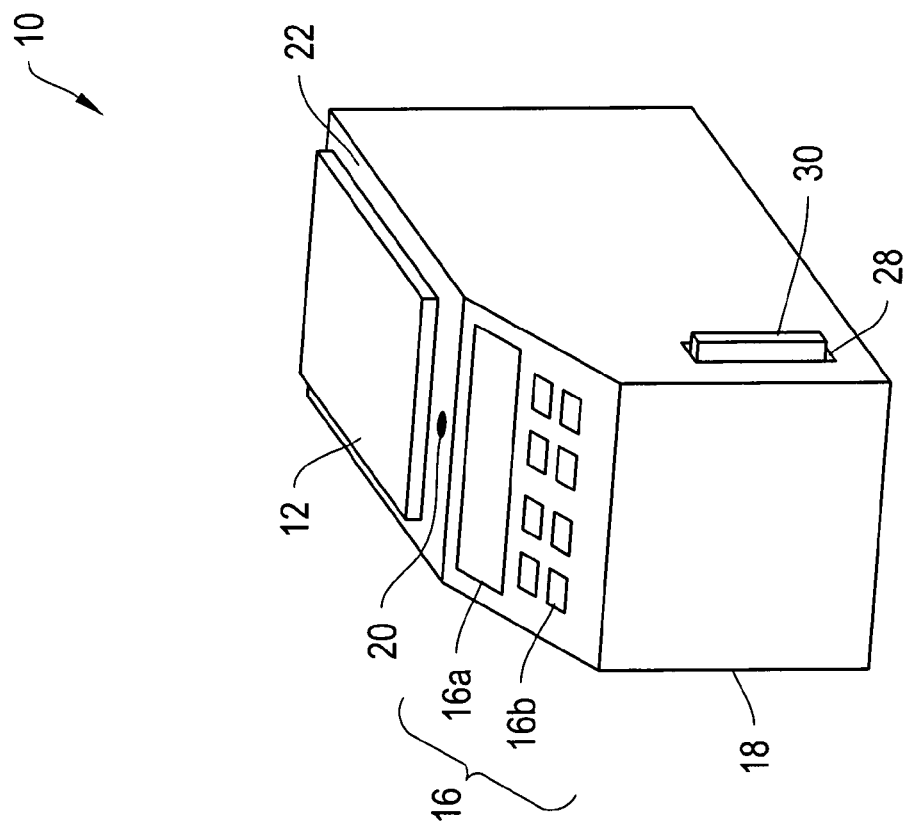
FIG. 1A depicts an exterior view of a benchtop apparatus for processing a sample according to an embodiment of the invention.

FIGS. 1A and 1B depict, respectively, an exterior view and an interior cross-sectional view of a benchtop ultrasonicator 10 for processing a sample 14 according to an embodiment of the invention. The ultrasonicator 10 is adapted for use by a single operator, and is generally sized to fit on and be supported by a table or bench in a laboratory setting. The ultrasonicator 10 can have a user interface 16 disposed on an outer housing 18, which can include a cover 12, or other access mechanism, for accessing the interior of the ultrasonicator 10. In particular, the access mechanism may allow access to a chamber within the outer housing 18.

The operator can access the ultrasonicator 10 by opening the cover 12. The cover 12 may open by detaching from the outer housing 18, by tilting on a hinge that attaches one side of the cover 12 to the outer housing 18, by sliding laterally along grooves that engage the cover 12 on the outer housing 18, by rotating in a lateral direction along a joint that attaches a corner of the cover 12 to the outer housing 18, or any other suitable mechanism. The mechanism may include one or more buttons, tabs, handles, latches, or catches that may be depressed, pulled, toggled, engaged/disengaged, or rotated to open and/or close the cover 12. Alternatively, the ultrasonicator 10 may be remotely controlled. For example, a USB or RS232 connector may link the ultrasonicator 10 to a robotic system that may, for example, use ActiveX control or any other suitable control protocol. In embodiments where the cover 12 slides laterally along grooves on the outer housing 18, the cover 12 may, for example, be disposed on the outer surface of the housing, or may be disposed in a recess within the housing 18. The mechanisms may be at least partially controlled electronically, such that the operator pushes a button on the user interface 16 or elsewhere on the outer housing 18 to open and/or close the cover 12. Although ultrasonicator 10 is depicted with the cover 12 being disposed on its top surface, one of skill in the art will recognize that other embodiments may additionally or instead have a door or cover 12 on a side of the outer housing 18, a drawer that slides laterally from the outer housing 18, or any other suitable mechanism for accessing the interior of the ultrasonicator 10. In certain embodiments, the ultrasonicator 10 may include a latch or other means for securing the cover 12 in a closed position during operation of the ultrasonicator 10. In certain embodiments, the ultrasonicator 10 may include a safety mechanism such that the device will not operate when the cover 12 is in an open position. In certain embodiments, the cover 12 in a closed position forms an air-tight seal with the outer housing 18, to permit pressurization of the treatment chamber relative to the surrounding atmosphere.

The cover 12 may be made of the same material as the outer housing 18, which can be made of any suitable material, such as plastic, glass, metal, etc. The interior of the cover may be lined with soundproofing material capable of dampening acoustic energy so as to reduce danger, disruption, or annoyance to the operator, e.g., to allow the device to operate quietly or silently in the perception of the user. The soundproofing material may be configured to absorb any acoustic energy that reaches it, or to reflect the acoustic energy back towards the sample 14. The outer housing 18 can be between about 5 centimeters and about 30 centimeters in width, height, or length.

In certain embodiments, a ultrasonicator 10 may include a sensor 20 on the outer housing 18 that triggers the cover 12 to open. The sensor 20 may be placed on the upper portion 22 of the outer housing 18, or any other suitable location, preferably selected to avoid accidental activation. The sensor 20 may include a motion detector configured to detect motion within a predetermined range, such as about 5 inches, so that the operator may move his/her hand or a sample 14 over the sensor 20 to trigger the cover 12, but motion further from the ultrasonicator 10 would not trigger the cover 12.

In certain embodiments, the sensor 20 may be configured to detect information about the sample 14. For example, the sample 14 could be labeled with a radio frequency identification (RFID) tag, text, a barcode, a symbol, or any other type of identifying mark, which sensor 20 could recognize using an RFID interrogator, optical recognition, acoustic recognition, or any other suitable means. In certain embodiments, the sample 14 could be marked using a special ink, a reflective material, or other distinguishing features that could be recognized using sensor 20.

Upon accessing the ultrasonicator 10, the operator may place the sample 14 within a sample holder 24 adapted to hold a sample vessel 26 containing the sample 14. Suitable sample vessels 26 include tubes, vials, aerosol vials, flasks, jars, bottles, wells, arrays, blister packs, ampoules, pouches, bags, envelopes, and other containers that are manipulable by the operator and capable of containing a sample under sonication conditions. In certain embodiments, the sample holder 24 can be a concavity or depression having a shape similar to an outer surface of the sample vessel 26, such that the sample vessel 26 can nest within the concavity or depression. The sample holder 24 can include a clamp, clip, or any other suitable fastener capable of holding the sample vessel 26 in place, e.g., around the neck of a flask or bottle, or around the body of a jar or tube. The sample holder 24 may also be configured to detect information about the sample 14. For instance, an adjustable clamp can encircle a test tube to both hold the test tube in place and measure the circumference of the test tube. A concavity or depression can be equipped with a scale to weigh the sample vessel 26 and sample 14. The ultrasonicator 10 may have other sensors or interrogation systems capable of detecting characteristics of the sample 14. For instance, the ultrasonicator 10 may detect an identifying mark, the location of the sample vessel 26, the level of fluid in the sample vessel 26, or any other initial characteristics of the sample 14. Other suitable characteristics and sensors are discussed in more detail below in reference to FIG. 2. The ultrasonicator 10 may also include a safety mechanism for determining that the sample 14 has been appropriately and securely positioned in the sample holder 24, such that the ultrasonicator 10 will not operate unless the sample 14 is appropriately and securely positioned.

In certain embodiments, the user may close the cover 12 manually. Alternatively, the ultrasonicator 10 may automatically close the cover 12, e.g., when the user activates the ultrasonicator 10 and/or when the ultrasonicator 10 determines that the sample is ready for sonication. The ultrasonicator 10 may also automatically devise and then execute a treatment protocol for the sample 14, or may prompt the operator to select or devise a treatment protocol using the user interface 16. The ultrasonicator 10 may also signal when the treatment protocol is finished, for example, by emitting an audio signal, turning an indicator light on or off, flashing or displaying a message on the user interface 16, or re-opening the cover 12.

The user, or operator, can use the user interface 16 to communicate with a control system of the ultrasonicator 10 which controls the operation of the ultrasonicator 10. Generally, the user interface 16 can query the user for input that may be communicated to a processor of the control system. The user interface 16 can include a display 16*a* to communicate information such as which treatment process options are available, the value of a particular setting, or data detected by any sensors the ultrasonicator 10 may have. The user interface 16 may also have buttons, dials, touchpads, knobs, sliders, or any other suitable control interfaces 16*b* with which an operator may indicate preferences, instructions, or parameters to the ultrasonicator 10. In one possible mode of operation of the ultrasonicator 10, the control system automatically devises and executes a treatment protocol upon detecting the presence of a sample 14 properly disposed within the ultrasonicator 10 and/or other sample characteristics, including any identifying marks. In another possible mode of operation, the user interface 16 prompts the operator to input information that the control system can use to select a treatment protocol. In one embodiment, the operator can manually configure a treatment protocol, for instance by selecting which waveform(s) to use, the duty cycle, the total energy, the relative positioning of the sample 14 to a acoustic energy source, and/or any other treatment parameters. In another embodiment, the operator can select a treatment protocol from a set of preprogrammed treatment protocols. The preprogrammed treatment protocols can be configured to each achieve a different objective or desired result, such as sterilization, mixing, reaction enhancement, and any other application of acoustic treatment. Each preprogrammed treatment protocol can also be configured to correspond to a particular sample, where the control system uses the characteristics of a particular sample either detected by sensors of the ultrasonicator 10 or from information entered by the operator via the user interface 16. In yet another embodiment, the operator can input information about the sample, such as the sample size, sample vessel, and desired objective or result, and then the control system automatically selects and executes a treatment protocol based on the information from the operator. The operator may also input acceptable ranges for any measured sample characteristics or parameters, such as temperature and pressure, which can help guide the control system's selection of a treatment protocol. In yet another embodiment, the operator can adjust the treatment protocol during the treatment process, for instance by lowering or raising the duty cycle, modifying the waveform, and/or switching to a different treatment protocol. The operator may also designate whether or not the treatment protocol should feedback information about the sample from sensors during the treatment process to adjust the treatment protocol. The control system can make feedback adjustments according to instructions from a preprogrammed treatment protocol and/or input from the operator. Further information about the control system is described below in reference to FIG. 3.

The user interface 16 can have an input mechanism that when activated initiates application of a focused acoustic field provided by the acoustic energy source to the sample 14. For example, the user interface 16 can have a pulse button that initiates sonication when the pulse button is pressed and stops sonication, for example, when the pulse button is released or pressed a second time. The parameters of the acoustic treatment can be preset by either the control system or the operator to a default treatment process, or may be selected by the operator at each use. The user interface 16 can have multiple pulse buttons, each corresponding to a different application, sample size, and/or treatment protocol.

In addition to allowing the operator to indicate his/her selections to the control system of the ultrasonicator 10, the user interface 16 can impart information to the operator, such as which treatment protocols and/or operating modes (e.g., feedback mode, fully automatic mode, etc.) are available to the operator. The user interface 16 can also display information measured, detected, or recognized by any sensors of the ultrasonicator 10, such as a sample ID from an identifying mark, sample temperature, or sample size. Information from sensors can be continuously displayed and updated during a treatment process to allow the operator to monitor the progression of the process. The control system may save the monitored data for later use or review by the operator. The saved data may be stored on a removable memory component compatible with a computer or other processing device. The ultrasonicator 10 may also be configured to produce hard copies of the data, such as a paper printout. The user interface 16 can also alert the operator, either through an audio or visual indicator such as a beeping sound, flashing light, or message within the display 16a, if the sample approaches or exceeds any boundaries defining an acceptable range for a sample parameter or characteristic. This combined monitoring/alert feature can be advantageous in embodiments or operating modes that do not use feedback to adjust the treatment protocol during treatment.

Treatment protocols and similar instructions for treating samples may be stored on a memory component 30 of the control system. In some cases it may be advantageous to store treatment protocols that are relatively specialized to specific uses, sample types, or objectives. The memory component may be fixed to the ultrasonicator 10, such as a silicon chip or other hardware component, or may be configured to be readily removable and exchanged for other memory components, e.g., such that the operator can select a memory component comprising treatment protocols pertinent to the needs of the operator. For example, if the ultrasonicator 10 is reallocated to a different use, a different memory programmed with protocols or other programs appropriate may be used in place of the original memory component. Similarly, as improved protocols are developed, the operator can also acquire newer memories including these improved protocols. The interchangeable memory component can be a memory card that slides through a memory card slot 28 on the outer housing 18. Alternatively, the memory card can be stored exterior to the outer housing 18, similar to a flash drive. Other suitable interchangeable memory components include compact discs (CDs), compact discs with read-only memory (CD-ROMs), digital versatile discs (DVD), diskettes, flash drives, and memory chips. In one embodiment, the ultrasonicator 10 can download treatments protocols from the internet, either onto an interchangeable memory component separable from the ultrasonicator 10, directly to a memory component built into the ultrasonicator 10, or to an ActiveX or other controller.

FIG. 1B depicts a cross-sectional view of the interior 44 of the benchtop ultrasonicator 10 according to an embodiment of the invention. The interior of the ultrasonicator 10 can have a cavity 32 specially shaped to fit around and hold a suitable sample vessel 26, such as a tube, that contains a sample 14. The cavity 32, or any other suitable sample holder, can be substantially surrounded by a first fluid bath 34 that is contained within a sample tank 36. The sample tank 36 can be suspended within a coupling medium, such as a second fluid bath 38, through which an acoustic energy source 40 may transmit acoustic energy to the sample 14. The second fluid bath 38 can be contained within an interior tank 42 of the ultrasonicator 10. The sample tank 36 and acoustic energy source 40 are capable of moving, and their positions may each be controlled by the control system of the ultrasonicator 10. At least a portion of the sample tank 36 can be made of a thin film material having low acoustic absorption and an acoustic impedance similar to the fluid within the second fluid bath 38. This portion of the sample tank 36 may be arranged so that it is aligned with the acoustic energy source 40.

In other embodiments, non-fluidic coupling means may be used. The acoustic energy can be transmitted through a viscous (semi-solid) layer 34 of, for example, silicone gel or rubber, or other material with a gel consistency or rubber consistency, which may optionally be sealed by an impervious membrane such as, for example, a plastic sheet or film, to form a laminate. Exemplary suitable sound-transmitting media are listed in Table 1. This list, however, should not be viewed as comprehensive and exhaustive, and other acoustic coupling media with adequate sound transmission properties may be used instead. In this arrangement, the sample vessel 26 may be pressed against the layer 34 for more efficient transfer of acoustic energy. In one embodiment, the cover 12 may be configured to provide this pressure by having an interior portion of the cover 12 disposed in contact with the sample vessel 26 when the cover 12 is closed, such that the sample vessel is pressed against the layer 34. To adjust for different sample vessel sizes while still applying pressure, the interior portion of the cover 12 may be coupled to a spring, bellows-like structure, or any other structure which can be compressed but also resists being compressed. Layer 34 may be free-floating on the fluid surface of fluid bath 38 or may be suitably supported in other ways, such as by making the membrane of the laminate of layer 34 in contact with fluid bath 38 more rigid, by a lattice frame (not shown) or the like.

Table 1 below lists the relative acoustic transmission of various materials relative to water (100%):

TABLE 1

| Material | Thickness (in mm) | Transmission at 1 MHz (in % relative to water) |
|---|---|---|
| No material (water) | | 100 |
| Acetate | 0.13 | 80 |
| Latex | 0.10 | 50 |
| PET (Mylar) | 0.13 | 90 |
| Silicone | 0.13 | 95 |
| PET (Mylar) | 0.05 | >95 |

Figure 2:
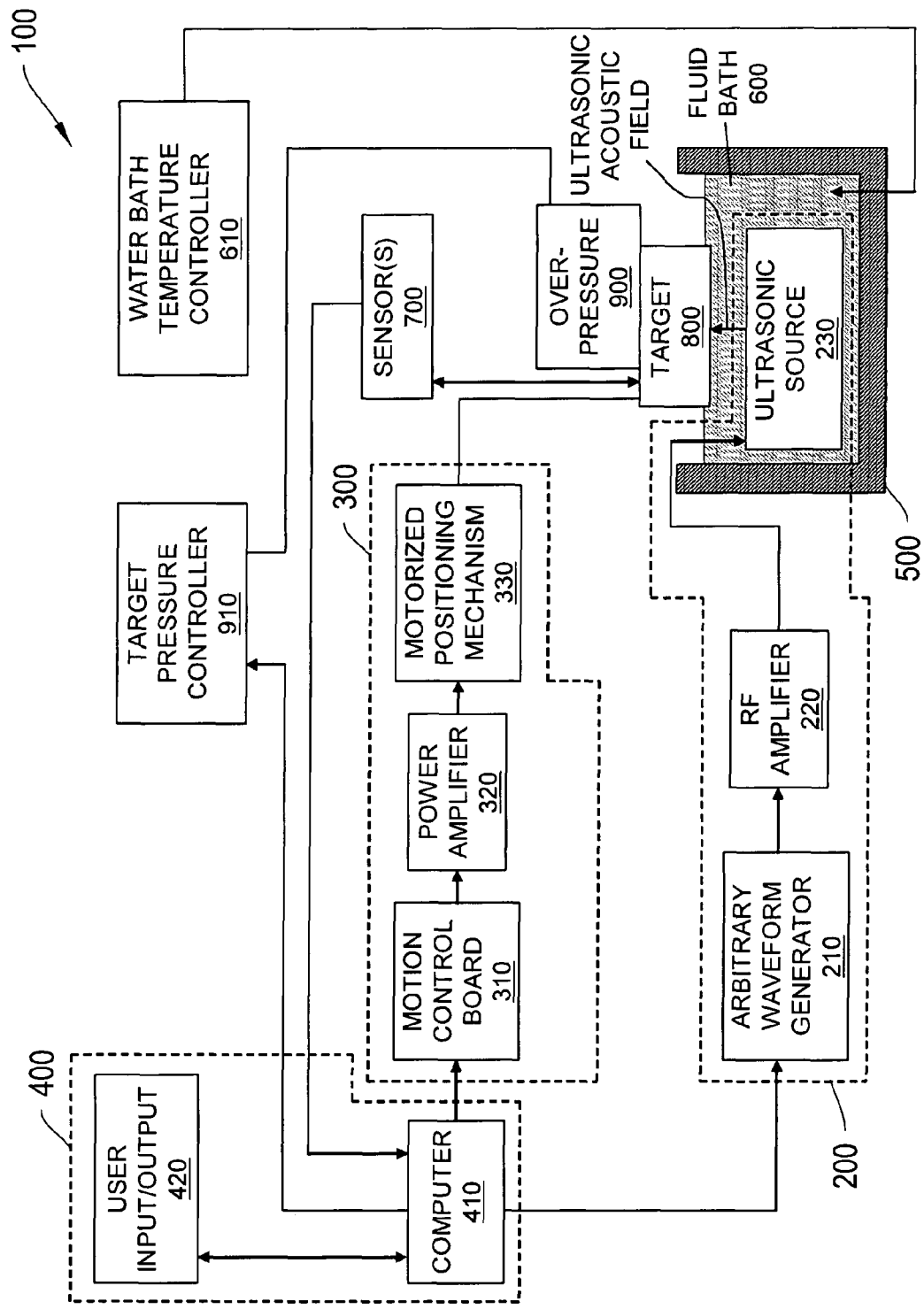
FIG. 2 is a schematic illustration of one embodiment of the apparatus according to an embodiment of the invention.

FIG. 2 depicts an electronically controlled ultrasonic processing apparatus 100 that includes an ultrasound treatment system and associated electronics 200, a positioning system 300 for the sample target 800 being treated, and a control system 400 which controls, generates, and modulates the ultrasound signal and controls the positioning system 300 in a predetermined manner that may or may not include a feedback mechanism. The source of acoustic energy 230 and the target 800 being treated are arranged in a fluid bath 600, such as water, such that the source of acoustic energy 230 is oriented towards the target 800. The target 800 may be positioned proximate the surface of the fluid bath 600, above the source of acoustic energy 230, all being contained within a sample processing vessel 500. Any of a multitude of sensors 700 for measuring processing parameters and/or recognizing sample characteristics can be arranged in or proximate to the fluid bath 600. A temperature control unit 610 may be used to control the temperature of the fluid in the fluid bath 610. An overpressure system 900 can control, for example, cavitation, by maintaining a positive pressure on the target 800 and may be adjusted, in a predetermined manner that may or may not include feedback processing, by a target pressure controller 910 that is connected to the control system 400.

Target 800 may be a sample, multiple samples, or other device, and may be contained in a variety of sample vessels. Sample vessels are sized and shaped as appropriate for the material to be treated, and can be any of a variety of shapes. For instance, a sample vessel can be an ampoule, vial, pouch, bag, or envelope. These and other sample vessels can be formed from such materials as polyethylene, polypropylene, poly(ethylene terephthalate) (PET), polystyrene, acetate, silicone, polyvinyl chloride (PVC), phenolic, glasses and other inorganic materials, metals such as aluminum and magnesium, and laminates such as polyethylene/aluminum and polyethylene/polyester. Certain configurations of a sample vessel can be made by vacuum forming, injection molding, casting, and other thermal and non-thermal processes.

An ultrasound acoustic field 240 can be generated by the acoustic energy source 230, for example, a focused piezoelectric ultrasound transducer, into the fluid bath 600. According to one embodiment, the acoustic energy source 230 can be a 70 mm diameter spherically focused transducer having a focal length of 63 mm, which generates an ellipsoidal focal zone approximately 2 mm in diameter and 6 mm in axial length when operated at a frequency of about 1 MHz. The acoustic energy source 230 is positioned so that the focal zone is proximate the surface of the fluid bath 600. The acoustic energy source 230 can be driven by an alternating voltage electrical signal generated electronically by the control system 400.

The positioning system 300 can include at least one motorized linear stage 330 that allows the target to be positioned according to a Cartesian coordinate system. The positioning system 300 may position and move the target 800 relative to the source 230 in three dimensions (x, y, z) and may optionally move either or both of the target 800 and the acoustic energy source 230. The positioning system 300 can move target 800 during and as part of the treatment process and between processes, as when multiple samples or devices within the target 800 are to be processed in an automated or high-throughput format. The positioning system 300 may position or move the target 800 in a plane transverse to the focal axis of the acoustic energy source 230 (x and y axes). The positioning system 300 can position and move the target 800 along the focal axis of the acoustic energy source 230 and lift or lower the target 800 from or into the fluid bath 600 (z axis).

The positioning system 300 can also position the acoustic energy source 230 and any or all of the sensors 700 in the fluid bath 600 along the focal axis of the acoustic energy source 230, if the sensors 700 are not affixed in the water bath 600, as well as lift, lower, or otherwise move the acoustic energy source 230. The positioning system 300 also can be used to move other devices and equipment such as detection devices and heat exchange devices from or into the fluid bath 600 (z axis). The linear stages of the positioning mechanism 330 can be actuated by stepper motors (not shown), which are driven and controlled by electrical signals generated by the control system 400, or other apparatus known to those skilled in the art.

Sensors 700 can be used prior to, during, or after the acoustic treatment to analyze the samples and/or detect certain physical properties of the sample, for example, by measuring responses to electromagnetic stimulation, such as optical spectroscopy, energy dispersion, scattering absorption, and/or fluorescence emission. Other measurable variables can include electromagnetic properties, such as electrical conductivity, capacitance or inductivity, as well as other physical parameters, such as sample uniformity or pattern analysis. Exemplary sensors may include an additional ultrasonic acoustic transducer suitable to transmit and/or receive an acoustic probe interrogation beam which can be used to assess one or more characteristics, such as the fill level, temperature, cavitation, homogeneity (e.g., presence of absence of particulate matter in the solvent, and/or the size of such particles), volume, etc., of the sample located within the sample vessel. It will be understood by those skilled in the art that the roles of the acoustic energy transducer 230 and the sensor transducer can be reversed in that the sensor transducer may operate to emit the acoustic processing beam while the transducer 230 performs sensing function. The system may include other types of sensors as well, such as an infrared (IR) temperature sensor to measure the sample temperature.

Interfaces, such as an interface between air and water, cause reflection of an incident ultrasound field. While reflection should be minimized for transmitting acoustic energy to the sample, a signal emitted from the acoustic energy source 230 or from a separate sensor and reflected by an interface, such as the meniscus of the sample within the sample vessel, can be used to quantify the height and therefore also the volume of the sample. In one embodiment, the sensor may be implemented as an acoustic transducer and emit a short burst of acoustic energy with a duration of 1 ms or less for interrogating the sample. Such short burst is also referred to as a "ping." As mentioned above, the interrogation burst can be focused on the sample. Due to reflection at the various interfaces encountered by the propagating interrogation sound wave, the sensor receives a return signal after a transit time proportional to the distance between the sensor and the respective interface. For example, it takes a sound wave approximately 10 ms to travel a distance of 1 cm, which is easily resolved by a detection system. The height location of the meniscus of the sample can then be determined from the arrival time difference between the sound wave reflected at the bottom of the sample, and the reflection at the liquid-air interface at the meniscus. The volume of the sample can be taken into consideration when applying acoustic energy for treatment of the sample.

Likewise, air bubbles and particulates can also block or reflect energy transmission through the sample volume. The same principle described above for determining the position of the meniscus can therefore also be used to evaluate the sample volume for the presence or absence of particulates, and/or the size and/or amount of such particles.

The control system 400 can include a computer 410, or other processor or microprocessor, and a user input/output device or devices 420 such as a keyboard, display, printer, etc. The control system is linked with the ultrasound treatment system 200 to drive the acoustic energy source 230, with the positioning system 300 to drive the stepper motors described above, with one or more sensors 700 to detect and measure process parameters and/or sample characteristics, and with one or more controllers, such as the target pressure controller 910, to alter conditions to which the target 800 is exposed. A fluid bath controller 610 could also be linked with the control system 400 to regulate temperature of the fluid bath 600.

The control system 400 can control and drive the positioning system 300 with the motion control board 310, power amplifier device 320, and motorized stage 330, such that the target 800 can be positioned or moved during treatment relative to the source 230 to selectively expose the target 800 to acoustic energy.

The control system 400 can specify a process to be performed upon a sample. In this regard, the ultrasound treatment system 200 can include an arbitrary waveform generator 210 that drives an RF amplifier 220, such that the acoustic energy source 230 receives an input. The output signal of the RF amplifier 220 may be conditioned by an impedance matching network and input to the acoustic energy source 230. The control system 400 can generate a variety of useful alternating voltage waveforms to drive a acoustic energy source. For instance, a high power "treatment" interval consisting of about 5 to 1,000 sine waves, for example, at 1.1 MHz, may be followed by a low power "convection mixing" interval consisting of about 1,000 to 1,000,000 sine waves, for example, at the same frequency. "Dead times" or quiescent intervals of about 100 microseconds to 100 milliseconds, for example, may be programmed to occur between the treatment and convection mixing intervals. A combined waveform consisting of concatenated treatment intervals, convection mixing intervals, and dead time intervals may be defined by the operator or selected from a stored set of preprogrammed waveforms. The selected waveform may be repeated a specified number of times to achieve the desired treatment result.

Figure 3:
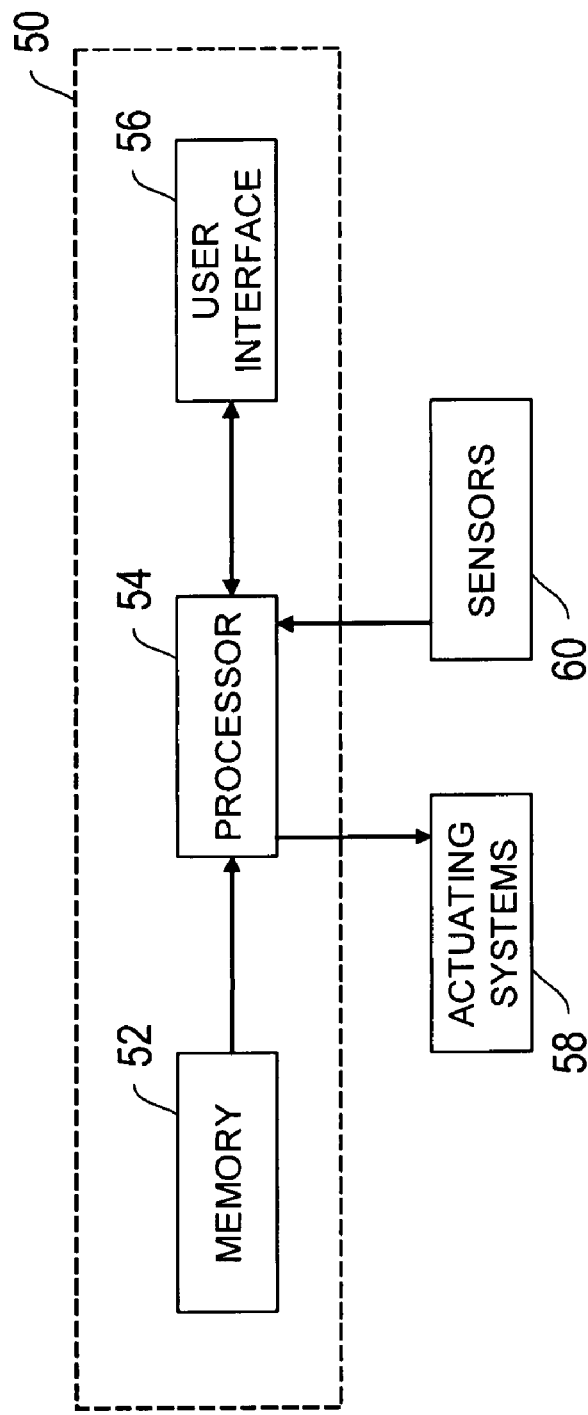
FIG. 3 is a schematic illustration of one embodiment of a control system according to an embodiment of the invention.
Figure 5D:
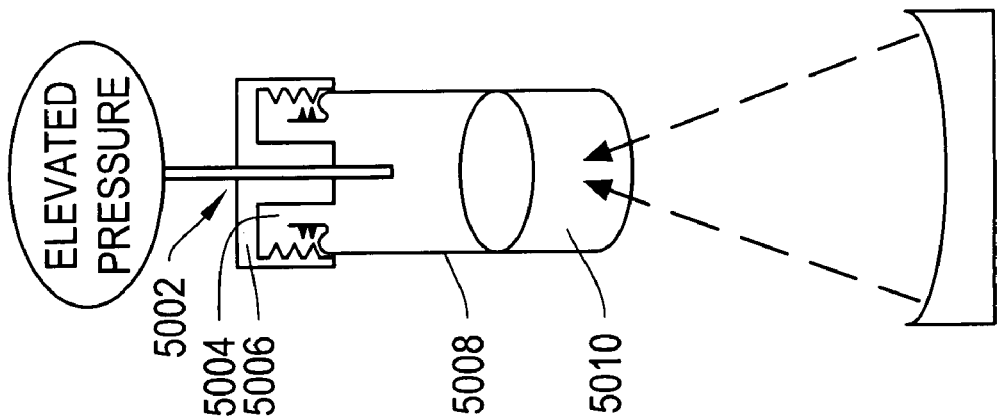
FIGS. 5A-5D depict an illustrative process for treating a pressurized sample with acoustic energy according to an embodiment of the invention.
Figure 5C:
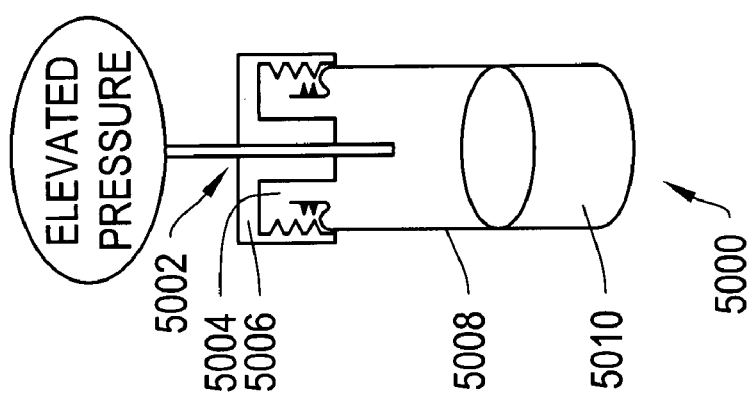
Figure 5B:
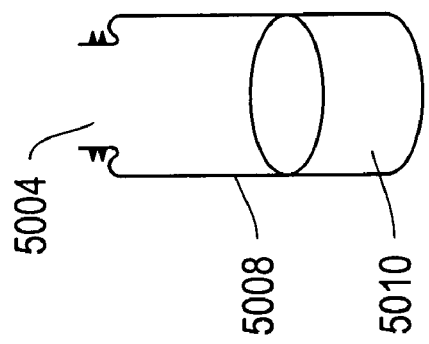
Figure 5A:
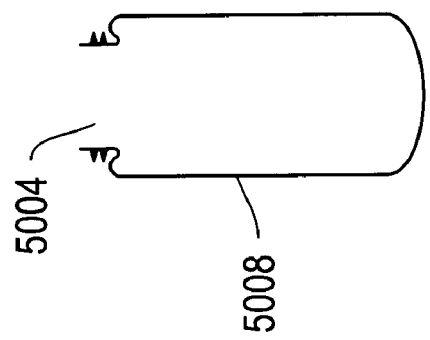

FIG. 3 depicts a control system 50 similar to control system 400 of FIG. 2 that includes a processor 54, a user interface 56, and a memory 52. The control system 50 links to actuating systems 58 that implement processes specified by the control system 50 and to sensors 60 that may measure processing parameters and/or detect sample characteristics. Actuating systems 58 can include positioning systems, ultrasound treatment systems for driving a acoustic energy source, parameter controllers, and any other devices capable of implementing treatment processes, such as those described above in reference to FIG. 1. Sensors 60 may monitor the impact and efficacy of a treatment process on a sample by detecting visual indicators, temperature, and/or cavitation. Sensors 60 may also detect initial characteristics of the sample like size, solubilization level, and type of sample vessel.

The memory 52 can include preprogrammed waveforms, protocols, and functions from which the processor 54 can select when determining a treatment process. Protocols can include combined or alternating waveforms and any other instructions for any actuating systems 58. The instructions are preferably predetermined to be advantageous for effecting a specific objective, such as enhancing a reaction, solubilizing the sample, or sterilization, for a specific sample type, which may be dependent on the sample contents, size, temperature, viscosity, level of solubility, vessel, or any other characteristics. Functions can configure a coordinated set of instructions for the actuating systems 58 or select a protocol based on input collected by the processor 54. The input can be initial characteristics of the sample and/or process parameters that can be detected by sensors 60 or entered by an operator via the user interface 42. For instance, a function can, given the volume and contents of a sample, determine the necessary waveform, duty cycle, and length of treatment to mix a sample without significant heating side effects. Other processing variables the function can determine include frequency, energy delivered, burst pattern, intensity, cycles per burst, pulse shape of the waveform, maximum energy level, etc. The processor 54 can select a process to implement based on a combination of user input from the user interface 42 and/or information from the sensors 60. The user interface 42 allows an operator to design and specify a process to be performed upon a sample. In particular, the operator can directly control instructions to actuating systems 58, select an option from the memory 52, indicate characteristics of the sample and an objective, or some combination thereof. The user interface 42 can also communicate to the operator which treatment process options are available and data detected by the sensors 60. Information from the sensors 60 can be used to configure a treatment process, to select a treatment process, or as feedback to a treatment process.

In one embodiment, measurable or discernible process attributes such as sample temperature, water bath temperature, intensity of acoustic cavitation, or visible evidence of mixing in the sample processing vessel, may be monitored by the control system 50 and employed in feedback loop to modify automatically during the treatment process any parameters controlled by actuating systems 58, such as the treatment waveform or acoustic energy source position. The modification of the treatment waveform may be a proportional change to one or more of the waveform parameters or a substitution of one preprogrammed waveform for another. For instance, if the sample temperature deviates excessively during treatment from a set-point temperature due to absorbed acoustic energy, the control system 50 may proportionally shorten the treatment interval and lengthen the convection mixing interval in response to the discrepancy between the actual and target sample temperatures. Or, alternatively, the control system 50 may substitute one predetermined waveform for another. The control system 50 may be programmed to terminate a process when one or more of the sensors 60 signal that the desired process result has been attained.

In another embodiment, initial characteristics of the sample may be used by the control system 50 to assess whether treatment is needed and/or to select a protocol or function optimized for those characteristics. Initial sample characteristics can include sample content, vessel, size, viscosity, temperature, pressure, and position relative to any of the actuating systems 58. In addition, one of the sensors 60 may be adapted to recognize an identifying mark either affixed to the sample or scanned in separately by the operator. The control system 50 may associate the identifying mark with a corresponding waveform, parameter, protocol, or function, e.g., such that the corresponding aspect of the treatment is set automatically by the controller upon detection of the mark and/or executed automatically upon activation of the ultrasonicator 10. If the computer has sufficient control over the effects of the actuating systems 58 to yield the desired objective, the use of a preprogrammed protocol or function may eliminate the need for monitoring sensors during the treatment process. In particular, the control system 50 upon recognition of sufficient sample characteristics can implement a protocol optimized to render the desired effect on that sample while maintaining the sample within certain constraints such as temperature or pressure ranges, without relying on feedback from sensors 60 while the process is in progress. An embodiment without process monitoring capabilities may be advantageous in cases where a simplified acoustic treatment apparatus is desirable, such as a benchtop apparatus for processing a single sample.

Acoustic treatment may be applied to many types of samples for a variety of purposes. Chemical and biological samples, as well as other types of samples, may be sterilized, mixed, or heated by acoustic treatment. Other applications are described in U.S. Pat. No. 6,719,449 entitled "Apparatus and Method for Controlling Sonic Treatment," which is hereby incorporated by reference herein. One application in particular is the acoustic treatment of blood or blood-based samples. Treatments can be configured to sterilize a blood sample, to ensure homogeneity of a blood sample, to mix a blood sample with an agent such as an anti-coagulant or a test compound that tests for antibodies, and any other suitable applications that may arise. The ultrasonicator 10, described above in reference to FIG. 1, can be adapted for blood treatment as well as for other applications, particularly applications involving small numbers or quantities of samples. In addition to clinical uses, the ultrasonicator 10 can be used in hospitals and doctor's offices to prepare or test blood or other samples.

Other applications outside of laboratory settings can utilize the agitating effects of acoustic treatment. Acoustic treatment may be used to break up and/or mix components during food or beverage preparation, to prepare cosmetics, and to homogenize mixtures/suspensions/solutions that separate or otherwise become heterogeneous during storage, such as paint. For instance, acoustic treatment can break up food at the cellular level and/or form emulsions or suspensions. Possible uses include making milkshakes, mayonnaise, purees, foams, sauces, juices (e.g., from fresh produce), ice cream, and butter. Acoustic treatment may be used to prepare cosmetics, such as lipsticks, moisturizers, creams, emollients, liquid soaps, perfumes, astringents, and other suitable colloidal or liquid products, or agitate paint to uniformly mix colors and components. The ultrasonicator 10 can be adapted for these non-clinical applications and be useful in settings in which customization and/or portability of the device is desired. For food preparation applications, the ultrasonicator 10 can be a countertop appliance in consumer or commercial settings, allowing a user to freshly prepare a customized food product. For cosmetic applications, customers in a retail setting can specify and mix colors, scents, and other ingredients for cosmetic products. For paint applications, the ultrasonicator 10 can allow a user to prepare paint for use. Due to the size and relative portability of the ultrasonicator 10, paint may be mixed at any desired location, for instance, by contractors or painters at a job site. The ultrasonicator 10 may also be used to create small samples of customized paint as an alternative to color swatches.

FIGS. 4 and 5 depict illustrative processes for treating a pressurized sample with acoustic energy. In particular, FIGS. 4A and 5A depict sample vessels for containing the sample and isolating it from other components of an acoustic energy apparatus. FIGS. 4B and 5B depict the sample vessels of FIGS. 4A and 5A, respectively, after samples have been deposited within the respective vessels. FIGS. 4C and 5C depict the samples and sample vessels of FIGS. 4B and 5B, respectively, after they have been sealed closed and pressurized to pressurize the samples. Methods and apparatus for pressurizing samples within sample vessels are described in more detail below. FIGS. 4D and 5D depict acoustic energy sources applying acoustic energy to the pressurized samples and sealed sample vessels of FIGS. 4C and 5C, respectively.

Without wishing to be bound by theory, by increasing the pressure of the fluid to be processed, the acoustic energy dose required to cavitate the solution may be greater. This may increase the shear forces consequent to cavitation bubble collapse. This may also result in greater retention time of the sample in the focal zone of the applied acoustic field and/or reduced rate of sample escaping the focal zone. This in turn may effectively increase the collision frequency of the sample with the acoustic bubbles generated by the applied energy and/or increase their resultant shear forces upon bubble collapse. Without wishing to be bound by theory, it is possible that the pressurization of the sample during the ultrasonic treatment may effect a transient increase in the effective viscosity of the sample, and that the acoustic energy has a greater effect in this altered state. This increase in effective strength may result in the observation of finer particle formation, faster tissue homogenization, accelerated lysis of microbial organisms, or otherwise provide for increased precision or speed of processing using the acoustic energy treatment process.

The sample may include a liquid or solution comprising a sample (e.g., tissue, cell, crystal, buffer, solvent, gel, gum, slurry, blend, single-walled carbon nanotubes, etc., or combination thereof). In certain embodiments, acoustic energy is applied to a solid sample, e.g., in a liquid or gaseous environment, to form particles of the solid material. For example, the application of focused acoustic energy to a solid can cause it to break apart into increasingly smaller fragments than unfocused acoustic energy. Similarly, acoustic energy can agitate sample pieces or particles, inducing collisions that promote further fracturing and/or fragmenting of the solids. In other embodiments, acoustic energy is applied to a liquid sample, thereby inducing the formation of particles. For example, acoustic energy can be applied to a supersaturated solution, causing a solute to precipitate out of solution. Alternatively, acoustic energy can be applied to a biphasic liquid sample, inducing mixing of the phases and causing the precipitation of a solid. Similarly, acoustic energy can be applied to a hot solution in conjunction with cooling, so that solids that precipitate during cooling are formed into particles of a desired size. The subject systems and methods can be applied to any procedure that results in the formation of a solid material in order to control the size and size distribution of the solid material that forms. Other procedures and desired results are described below.

An additional benefit for a system is that the entire acoustic circuit, which in some embodiments includes a series of acoustic interfaces such as the transducer-couplant, couplant-vessel, vessel wall, vessel-inner sample, and sample-air/vapor headspace, may be pressurized, which may improve the efficiency of the treatment process. For example, just as a more dense acoustic couplant may transmit acoustic energy more efficiently, a pressurized fluid may transmit acoustic energy more efficiently than a non-pressurized fluid.

FIG. 6 depicts an illustrative process for treating a pressurized sample with acoustic energy. In addition, FIG. 6 allows higher pressures to be obtained readily without requiring a special vessel, materials, or a custom design. In particular, FIG. 6A depicts an acoustic energy treatment system which includes an acoustic energy source 6002 coupled via a coupling medium 6004 to a sample vessel 6006 containing a sample 6008, similar to the sample vessel 4010 depicted in FIG. 4B. The medium 6004 may be a fluid, such as water or buffer, or other compressible medium. FIG. 6B depicts the system of FIG. 6A after it has been placed within an air-tight chamber 6010 and pressurized. More particularly, both the sample 6008 and the medium 6004 coupling the acoustic energy source 6002 to the sample vessel 6006 are pressurized due to the elevated atmospheric pressure within the chamber 6010. Methods and apparatus for pressurizing acoustic energy treatment systems are described in more detail below.

FIG. 6C depicts the acoustic energy source applying acoustic energy 6012 via the pressurized medium 6004 to the pressurized sample 6008.

The pressurizing atmosphere may be compressed air, nitrogen, argon, helium, or any other suitable gases or combination thereof. Certain gases may be preferred in certain applications, e.g., for their intrinsic physical properties such as inhibiting biological events, such as nitrogen, or because they may beneficially alter the cavitation threshold energy, such that an altered headspace over a fluidic or partially fluidic/solid sample more readily enables bubble formation and collapse.

In various embodiments, certain vessel designs may be used to apply pressure to a sample. These vessel designs may allow a lab technician to apply pressure to a sample efficiently so that multiple samples can be processed with minimal time and effort. For example, a sample vessel may have a sealing mechanism, for sealing the interior of the sample vessel from the external atmosphere, with which the lab technician, or any other user, may pressurize the sample.

In one embodiment, an acoustic energy apparatus processes a single sample, e.g., which is inserted into the device. Alternatively, a collection of samples may be inserted into the device, e.g., in a suitable rack, container, or other array for holding the collection of samples. In either scenario, a sealing cap is applied to an individual sample to simultaneously close and pressurize the sample. For example, the sealing cap, while engaging the vessel containing the sample, acts as a piston to pressurize the sample. FIG. 4C depicts an exemplary sealing cap 4002 for pressurizing a sample 4004. In particular, the sealing cap 4002 has a bayonet portion 4006 encircled by a rim 4008 of approximately the same length as the bayonet portion 4006. The size and shape of the rim 4008 is selected such that when the sealing cap 4002 initially engages the sample vessel 4010, the rim 4008 seals off exposure of the sample 4004, and the rest of the vessel interior 4012, to the environment external to the vessel 4010. As the sealing cap 4002 is further engaged with the vessel 4010, such that the rim 4008 overlaps more of the walls of the sample vessel 4010, the bayonet portion 4006 protrudes into the vessel interior 4012 to increase the pressure within the vessel 4010, thereby pressurizing the sample 4004. Generally, a sealing mechanism may include a displacement portion, such as the bayonet portion 4006, that can protrude into the interior of the sample vessel to decrease the volume of the interior, thereby pressurizing the sample contained within the interior.

Alternatively, a sample may be sealed and then pressurized after sealing. For example, FIG. 5 depicts an embodiment of a vessel 5000 used to apply pressure to sample or samples 5010. The vessel chamber 5008 may be accessed through input 5004. Input 5004 may be covered by a protective seal 5006 that is bonded or engaged with vessel chamber 5008. Protective seal 5006 may be reversibly sealable so that sample or samples 5010 can be introduced into vessel chamber 5008. Protective seal 5006 may be made from any combination of metal, glass, plastic, rubber, plastic film, or any other material suitable to form a bond with vessel chamber 5008 in order to provide a seal, e.g., to prevent sample from exiting the chamber during treatment. In certain embodiments, the seal may be air-tight, water-proof, and/or hermetic. Vessel chamber 5008 may be made from any combination of metal, glass, plastic, rubber, plastic film or any other suitable nonporous material that enables vessel chamber 5008 to provide a barrier between the sample or samples 5010 and an external environment. In certain embodiments, protective seal 5006 may comprise port 5002. Port 5002 may be a reversibly sealable port, such as a one-way valve or a rubber septum, for accessing the vessel chamber 5008, e.g., for supplying pressure to vessel chamber 5008, and thus sample or samples 5010. In one embodiment, port 5002 may be shaped and sized to interface with a needle, such as a hypodermic needle, air injector, cannula, or similar feature. The needle may be used to add or remove materials, such as a sample, a liquid, or a gas, to or from the vessel chamber. In certain embodiments, the vessel chamber may be pressurized (e.g., with air, argon, nitrogen, or another suitable gas) prior to the introduction of the sample or sample medium via a needle. In other embodiments, a needle may be used to inject a liquid or gas into vessel chamber 5008 after introduction of the sample in order to increase the pressure within vessel chamber 5008. For example, the liquid or gas so introduced may be an inert gas, compressed air, a solvent for the sample, or a suitable treatment medium for the sample. In certain embodiments, the needle may be coupled to a mechanical or manual air pump to increase the pressure of the environment within vessel chamber 5008. For example, in certain embodiments, the needle may be attached to a bulb. The bulb may be made out of a malleable and durable material such as rubber, plastic, or any other suitable material that is able to deform nondestructively and preferably reversibly when mechanically squeezed. The bulb may be shaped and sized so that the volume of the bulb is greater than the volume of the vessel chamber 5008. In certain embodiments, the bulb may be squeezed or otherwise deformed to inject a liquid or gas into vessel chamber 5008 in order to increase the pressure within vessel chamber 5008. Thus, vessel 5000 permits sample or samples 5010 to be exposed to higher pressures in order to facilitate processing of the sample or samples.

Figure 7:
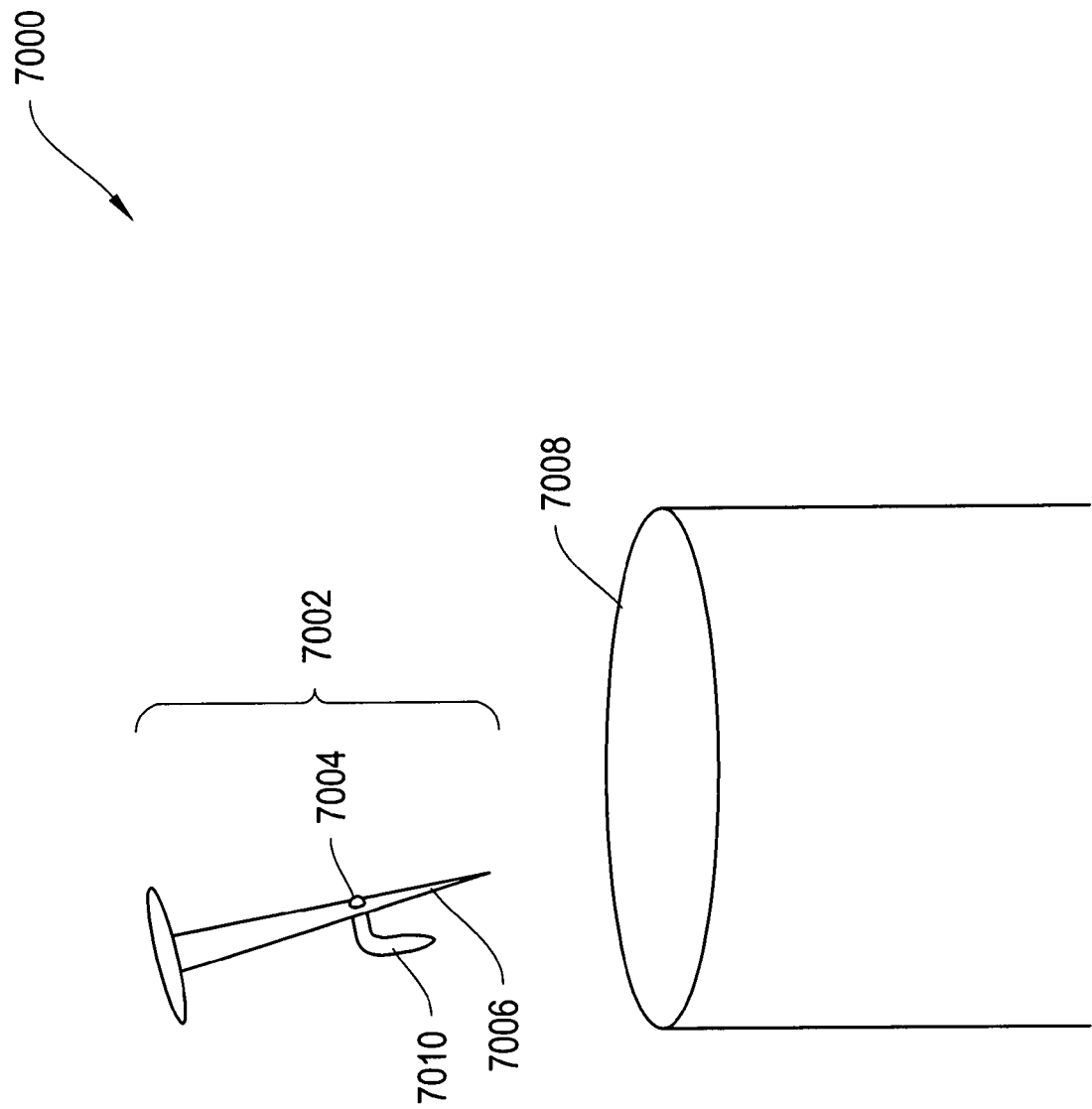
FIG. 7 depicts an illustrative pressurizing device according to an embodiment of the invention.

FIG. 7 depicts an embodiment of an automatic pressurizing device 7002 to increase the pressure of the environment within a sealed vessel chamber, such as the sealed vessels of FIG. 5. The device includes a needle 7006 adapted to reversibly penetrate a seal, such as a rubber septum, a gas source 7008, (e.g., a canister of compressed air, nitrogen, argon, or other suitable gas or mixture thereof), and optionally a pressure sensor 7004. Pressure sensor 7004 measures the pressure of the environment at the end of the needle 7006, and may be mechanical or digital. Digital pressure sensors may include piezoresistive semiconductors, microelectromechanical system chips, variable capacitors, or other hardware to suitably detect the pressure of an environment. In embodiments that include pressure sensor 7004, the automatic pressurizing device 7002 may be configured to automatically pressurize the chamber in an automated fashion when the needle 7006 is inserted into a sample until a desired level of pressure is reached within the sample chamber. In such embodiments, the automatic pressurizing device 7002 may be triggered by the force exerted on the needle when it is pushed through a septum, or it may be triggered by force applied to a trigger external to the needle 7006. The trigger may comprise, for example, a guard 7010 in the vicinity of the needle that contacts the septum as the needle penetrates the septum, or a manual trigger such as a button or lever operated by the user (not shown). Upon activation, the automatic pressurizing device 7002 may add gas to the chamber until a predetermined pressure is reached, e.g., the pressure of the gas source 7008, or a pressure set by the user or the manufacturer of the device, e.g., via an interface (not shown). In embodiments employing a pressure sensor 7004, the pressure sensor 7004 may communicate with a controller that can operate to open or close a pathway between the gas source 7008 and the needle 7006 so that the correct amount of pressure is reached in a vessel chamber. This communication may occur through electrical means, such as a wire, RFID, or wireless communication, or any other suitable means.

In an exemplary embodiment, a sample vessel may be sealed with a pierceable septum. For example, the sample may be contained within a 13 mm×65 mm round bottom borosilicate glass culture tube (Chromocol, UK) with a screw cap end that is sealed with a Bakelite cap having a rubber septum center. A needle, such as a 22-gauge, 1.5-inch hypodermic needle, can be inserted through the septum to apply elevated pressure through the needle. The pressure equilibrates through the needle bore, pressurizing the interior of the tube and the sample. High-intensity focused ultrasound ("HIFU") acoustic energy (as used with the Covaris, Woburn, Mass., USA S-series instruments) can then be applied to process the sample in the tube. The pressure may be allowed to equilibrate to atmospheric pressure, and then the sample may be removed from the tube, e.g., by inserting the needle further into the tube to collect the fluidic sample in a manual manner. Alternatively, the pressure in the tube may be used to eject the sample, e.g., through a cannula inserted through the septum into the sample. All or part of the above-described process, including sample preparation, sealing, pressurization, treatment, depressurization, and sample removal, may be readily automated. In some such embodiments, the needle, though inserted into the sample chamber, is not in the focused acoustic energy field. In other embodiments, the needle may be located in the acoustic focal zone, e.g., as a nucleation site for cavitation events.

In another embodiment, a single sample or a batch of single samples are inserted into an apparatus and pressurized prior to the application of acoustic energy. For example, a microtitre plate with 96 350-microliter sample wells may be loaded with 100 microliters per well. The open plate may be inserted into an apparatus which allows the atmosphere at the fluid/air interface of the samples to be elevated prior to an acoustic dose. Alternatively, the plate may be sealed prior to treatment with a lid that either pressurizes each well (e.g., via a piston-type approach, as discussed above) or allows the sealed compartment to be pressurized (e.g., through a septum or one-way valve, as discussed above).

In another embodiment, a sample vessel may have one or more flexible or elastic walls to allow the volume of the interior of the sample vessel to decrease, thereby increasing the pressure. One of the walls, or portion of a wall, of the sample vessel may be sufficiently pliable to allow increased pressure external to the pliable wall to be transmitted to the contained sample. For example, a plastic bag, a balloon, a test tube having a slidably engaged piston plunger, or other sample vessel having a deformable structure may shrink in volume when placed in an elevated pressure atmosphere, thereby pressurizing the sample, even though the sample remains sealed from the external environment. Alternatively or in addition, an external force may be applied to the sample vessel to shrink the volume of the vessel interior. The application of the external force may be automated or may comprise a user of an acoustic treatment apparatus physically manipulating the sample vessel to deform its structure.

Figure 8:
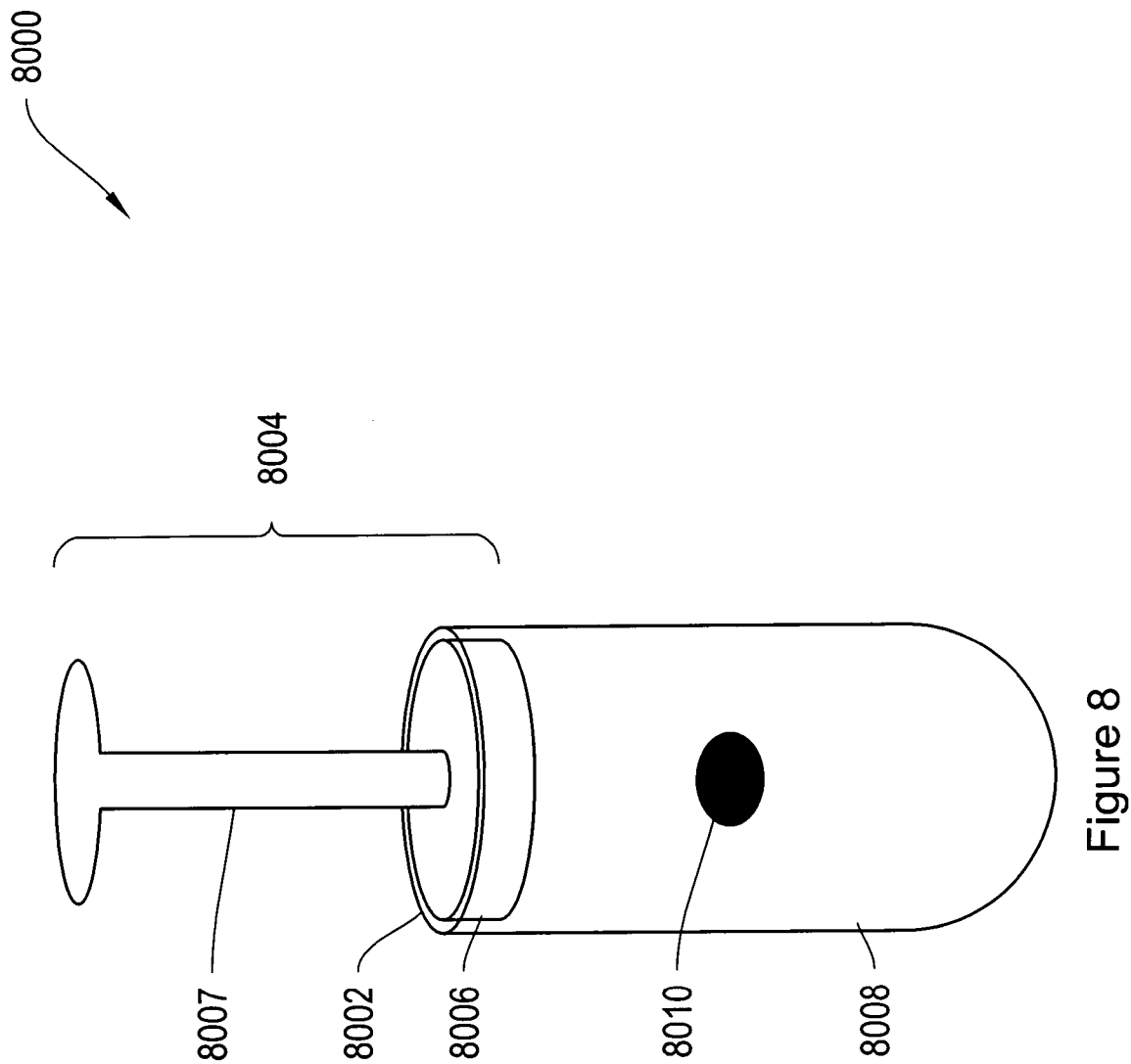
FIG. 8 depicts an illustrative vessel according to an embodiment of the invention.

FIG. 8 depicts another embodiment of a vessel 8000 used to apply pressure to sample or samples 8010. The vessel chamber 8008 may be accessed through input 8002. Vessel chamber 8008 may be made from any combination of metal, glass, plastic, rubber, plastic film or any other suitable nonporous material that enables vessel chamber 8008 to provide a barrier between the sample or samples 8010 and an external environment. Input 8002 may be shaped and sized to interface with plunger 8004. Plunger 8004 may comprise a stopper 8006 coupled to a stem 8007. The length of stem 8007 of plunger 8004 may be equal to or greater in length than the length of vessel chamber 8008, but is typically sufficiently long to facilitate movement of the stopper 8006 through a range of positions within the vessel chamber. Stopper 8006 of plunger 8004 may be shaped and sized to form a seal with input 8002. Stopper 8006 of plunger 8004 may be made out of rubber, plastic, or any other suitable material to form a seal with input 8002. The seal is preferably airtight. Stem 8007 of plunger 8004 may be made out of glass, plastic, or any other suitable material that allows a user or an automated device to employ stem 8007 of plunger 8004 and deliver a downward force to reduce the volume of the vessel chamber 8008, thereby increasing the pressure in the chamber. Stem 8007 of plunger 8004 may also be shaped and sized so that it may be employed to apply an upward force to remove stopper 8006 from the vessel chamber 8008 so that the pressure within vessel chamber 8008 may be reduced and/or the vessel chamber can be accessed. Thus, vessel 8000 may be employed to expose sample or samples 8010 to higher pressures in order to facilitate processing of the sample or samples.

Figure 9:
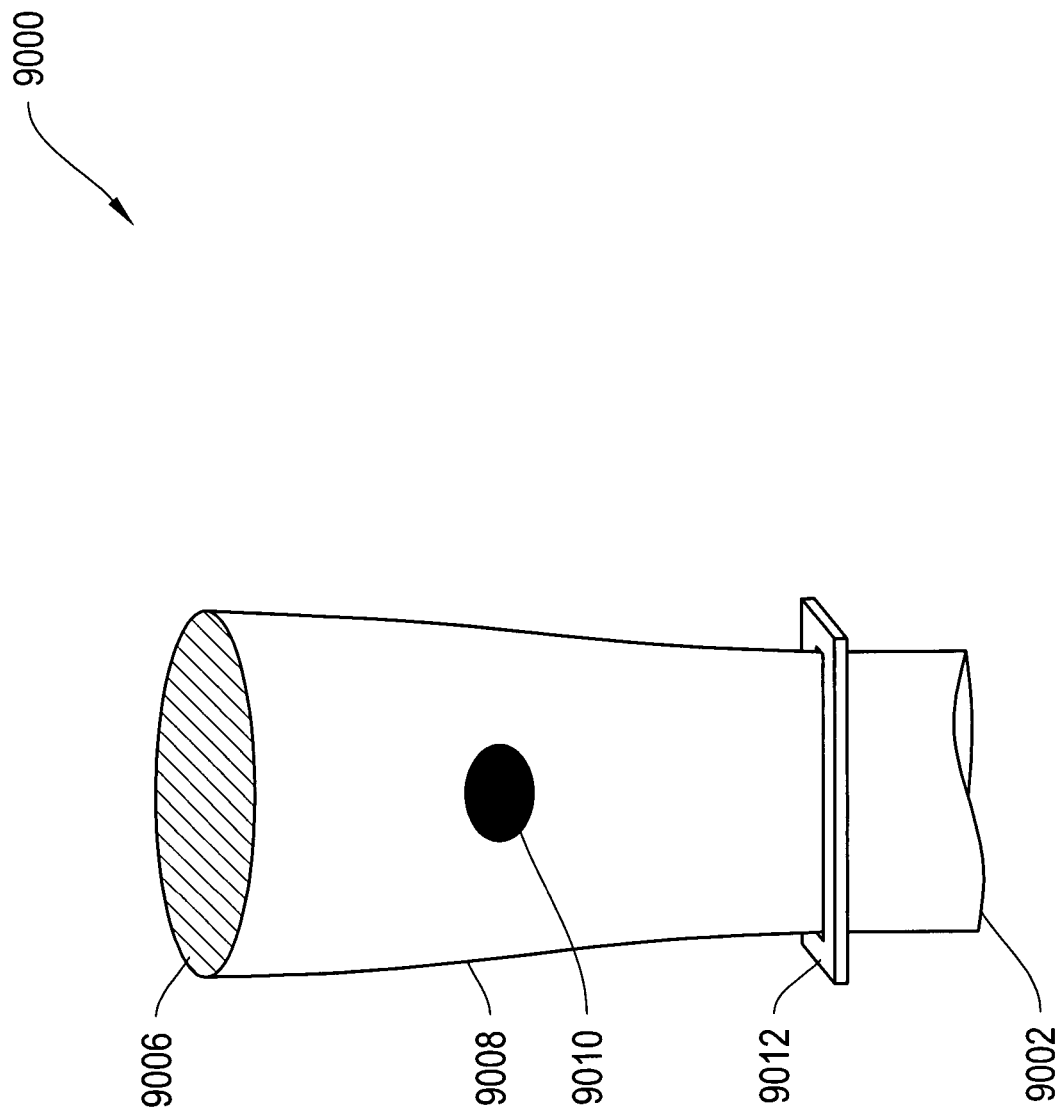
FIG. 9 depicts an illustrative vessel according to an embodiment of the invention.

FIG. 9 depicts another embodiment of a vessel 9000 used to apply pressure to sample or samples 9010. Sample or samples 9010 may be placed inside vessel chamber 9008 through input port 9002. Vessel chamber 9008 may be made out of a substantially malleable yet durable material such that vessel chamber 9008 deforms nondestructively when physically manipulated and provides a barrier between the sample or samples 9010 and an external environment. Suitable materials include rubber, metal foil (e.g., aluminum), plastic, or any combination thereof. Vessel 9000 also includes bottom 9006. Bottom 9006 may be shaped and sized to fit into a sample holding device such as a 96-well plate, or any suitable sample holding device. In certain embodiments, input port 9002 may be shaped and sized to be clamped by clip 9012. Clip 9012 may be made out of plastic, rubber, or any material suitable to clamp input port 9002. Clip 9012 may be shaped and sized to slide up and down the body of the vessel chamber 9008 and hold a fixed position after movement. Clip 9012 may be removable (e.g., to access vessel chamber 9008 through input port 9002), and preferably seals vessel chamber 9008, e.g., for treatment, such as with an airtight seal. In a variant embodiment, input port 9002 may be located on the side of the vessel 9000, such that the clip 9012 slides up and down the body and over the port 9002, thus reversibly sealing the vessel chamber 9008. By manipulating clip 9012, parts of the vessel body 9008 may deform nondestructively. In certain embodiments, manipulating clip 9012 may reduce the volume of vessel chamber 9008. By reducing the volume of vessel chamber 9008 in this manner, the vessel chamber 9008 may be pressurized. Thus, vessel 9000 may be employed to expose sample or samples 9010 to higher pressures in order to facilitate processing of the sample or samples.

In another embodiment, focused acoustic energy is applied to a flowing fluid stream exposed to elevated pressure prior to and/or during acoustic energy treatment. This embodiment may form part of a flow-through or intermittent flow system that may be employed in the production of fine chemicals, food products, pharmaceuticals, cosmetics, and in other manufacturing settings. For example, this system may include a cell with a quartz window for acoustic energy transmission. In another example, the flowing fluid stream passes through a constriction which elevates the pressure on the fluid in the region preceding the constriction. The entire transducer may be contained within the flowing stream of a sample to be processed that is intermittently pressurized. In certain embodiments, a focused acoustic energy apparatus may synchronize the flow with the acoustic dose to achieve the desired result (e.g., crystal dissolution, sonocrystallization, and the like). This continuous flow process may also be automated.

Various embodiments of the present invention will be further understood by reference to the following non-limiting examples.

EXAMPLE ONE

Long nucleic acid strands, such as genomic DNA, are too large to use in certain applications without first shearing the strands to fragments of smaller size, e.g., for library construction or for certain methods of DNA sequencing. Cleaving the DNA strands to fragments with lengths of 500 base pairs ("bp"), 200 bp, or less can thus be an important step in the preparation of DNA samples.

In this example, 20 µg of lambda DNA in 400 µl of 1 mM EDTA was placed in 13×65 mm round bottom glass tubes. Each tube was then treated in an S2 turbo at 10% duty cycle, 10 intensity, and 200 cycles/burst for 6 minutes in the power track mode with a bath temperature of 7-8° C. The treatments were conducted at or near the following pressures: 14.7 pounds per square inch ("psi"), 29 psi, 44 psi, and 57 psi. The sizes of the DNA fragments were then determined by running 22 µl aliquots from each tube on a 0.7% agarose gel along with size markers. The DNA was visualized with ethidium bromide staining. The size of the starting lambda DNA was 48,502 bp. After treatment at 14.7 psi, the majority of the DNA fragments were in the 100 to 650 bp size range. After treatment at 29 psi, the majority of the DNA fragments were in the 100 to 500 bp size range; and at pressures of 44 and 57 psi, the majority of the DNA fragments were in the 100 to 375 bp range, as summarized in Table 1 below.

TABLE 1

Ranges of sizes for the majority of DNA fragments after treatment at various pressures

| Pressure | DNA Fragment Sizes |
|---|---|
| 14.7 psi | 100-650 bp |
| 29 psi | 100-500 bp |
| 44 psi | 100-375 bp |
| 57 psi | 100-375 bp |

EXAMPLE TWO

The DNA shearing described in example one may also be controlled by the variation of the pressure level, e.g., 1, 2, and 3 atmospheres ("atms") and beyond. A dose response was observed by variations in the pressure of the sample while keeping the treatment duration, temperature, and acoustic dose constant In this example, 20 µg of lambda DNA in 400 µl of 1 mM EDTA was placed into 13×65 mm round bottom glass tubes. Each tube was then treated as in Example One, except that only pressures of 14.7 psi and 44 psi were used. Aliquots of 22 µl were removed after 1, 3, and 6 minutes of treatment. The size of DNA fragments was determined by agarose gel electrophoresis as in Example One. At 14.7 psi, the size ranges for the majority of the DNA fragments at various treatment durations are summarized by Table 2 below.

TABLE 2

Range of sizes for the majority of DNA fragments after treatment at various durations and pressures

| Treatment Duration | DNA Fragment Sizes with Treatment at 14.7 psi | DNA Fragment Sizes with Treatment at 44 psi |
|---|---|---|
| 60 seconds | 200-2,000 bp | 150-1,000 bp |
| 180 seconds | 100-1,000 bp | 100-500 bp |
| 360 seconds | 100-700 bp | 100-375 bp |

EXAMPLE THREE

Particle generation of hydroxyapatite (HAP) may be faster and result in smaller particles. Treating crystals while at elevated pressures may produce more and smaller fragments at a faster rate.

A suspension of ceramic hydroxyapatite particles was prepared by placing 3.1 mg of ceramic hydroxyapatite particles (20 µm from Bio-Rad, Hercules, Calif.) in a 13×65 mm glass round bottom screw cap tube and adding 2.0 ml of 50 mM trisodium citrate. The tube was capped and immediately processed in a Covaris S2 instrument with the following treatment parameters: power track mode, water bath temperature 8 degree C., 10% duty cycle, 10 intensity, 200 cycles per burst, and 30 seconds of treatment. The contents of the glass tube were then transferred to a cuvette and left undisturbed for 300 seconds to allow any large particles present to settle out. The cuvette was then placed in a spectrophotometer and the absorbance at 600 nm measured. The absorbance is due to light scatterings by the small particles that remain in suspension and thereby provides a measure of the amount of small particles generated by the acoustic treatment.

For the elevated pressure experiments, the cap of the 13×65 mm tube was fitted with a tubing connection and a section of Tygon tubing that connected the glass tube to a pressure regulator that was, in turn, connected to a compressed air supply. Control experiments run at atmospheric pressure (approximately 15 psi) had an absorbance reading of 0.699 after 30 second of the above treatment. Experiments at elevated pressure were run at approximately 45 psi with compressed air and had an absorbance reading of 1.442 after 30 seconds of acoustic treatment. Thus the rate of fragmentation during the first 30 seconds of acoustic treatment was doubled when the pressure was increased to 45 psi.

EXAMPLE FOUR

Yeast spores are more readily disrupted with the elevated pre-pressurization prior to application of focused acoustic energy. This pressurization may render the spores more susceptible to the effects of HIFU. Treating yeast while at elevated pressures may increase the lysis of yeast cells.

Yeast cells from a frozen stock were suspended in 1.5 ml of 33 mM potassium phosphate pH 7.5 buffer in a 13×65 mm glass round bottom screw cap tube. 25 µl of a lyticase (Sigma, St. Louis, Mo.) stock (500 units/ml in cold distilled $H_2O$ made fresh daily) was added to the tube. The tube was capped and processed with a Covaris S2 instrument. The acoustic treatments were run in the power tracking mode with a water bath temperature of 26+/−1 degree C. The control sample was run at atmospheric pressure with brief low power acoustic mixing to keep the yeast cells in suspension. The low power treatment parameters were as follows: 1% duty cycle, 3 intensity, 200 cycles per burst, for 10 seconds; then 1% duty cycle, 0.1 intensity, 50 cycles per burst, for 50 seconds. These steps were repeated to generate the selected total treatment time. The parameters for high power treatment were: 20% duty cycle, 10 intensity, 200 cycles per burst, 30 seconds; then 1% duty cycle, 0.1 intensity, 50 cycles per burst 60 seconds; and again 20% duty cycle, 10 intensity, 200 cycles per burst, 30 seconds. For the elevated pressure experiment the pressure in the tube was increased to 45 psi as described in Example 3 above. 60 µl aliquots were removed from the glass tubes at selected time intervals and transferred to a 0.65 ml microcentrifuge tube. The tube was centrifuged at 10,000 rpm for 1.5 minutes to pellet the cells; 50 µl of the supernatant was assayed for soluble protein using the Bradford dye binding assay (the absorbance at 595 nm is proportional to the protein concentration).

Figure 10:
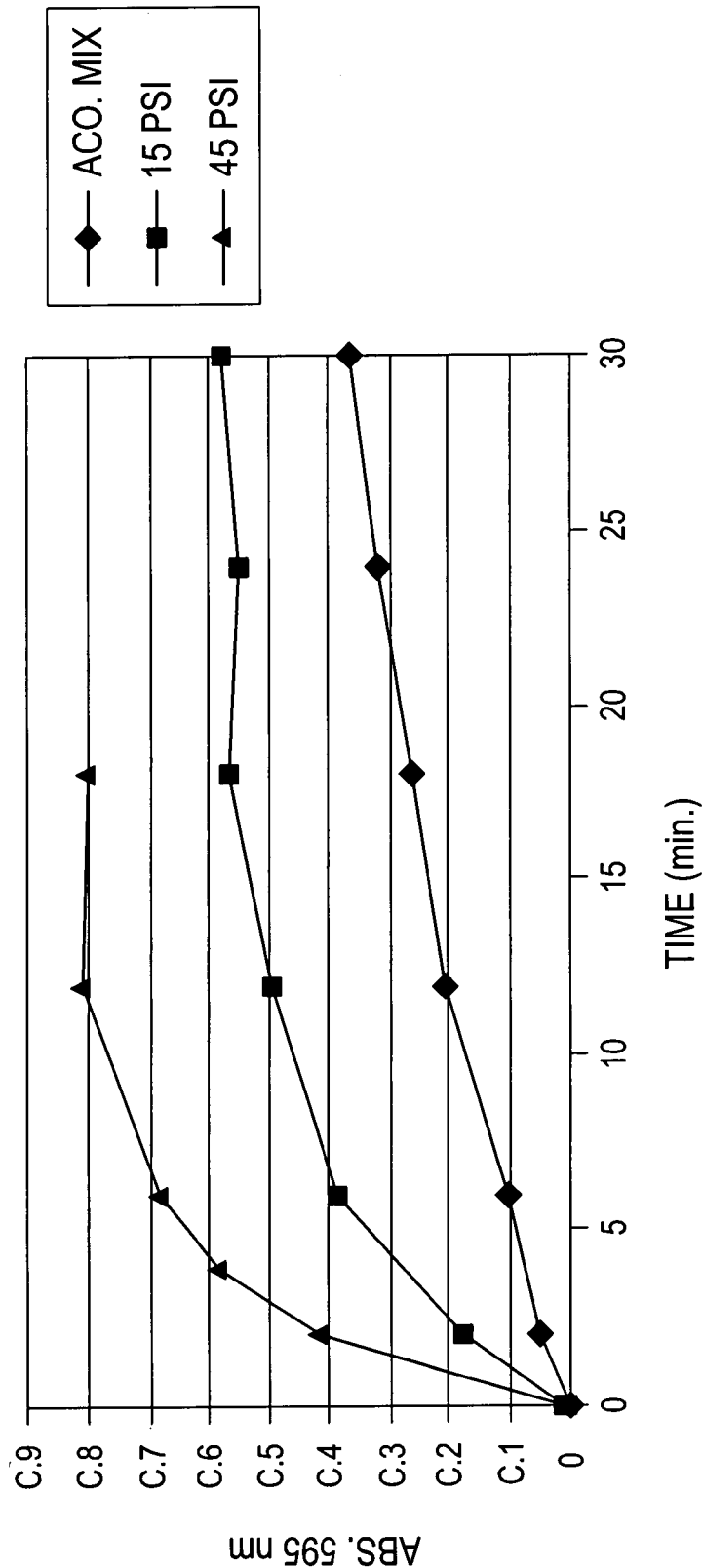
FIG. 10 depicts a graph of the absorbance of yeast samples after treatment at various durations, pressures, and acoustic intensities.

FIG. 10 depicts a graph showing absorbance of yeast samples after acoustic treatment at various durations, pressures, and acoustic intensities. The line labeled "Aco. Mix" represents results from using an acoustic mix that was low power and sub-cavitation energy to gently resuspend yeast during incubation. The line labeled "15 psi" represents results from using a high power focused acoustic field at atmospheric pressure. The line labeled "45 psi" represents results from using a high power focused acoustic field at elevated pressure.

After two minutes of treatment, as shown in the graph depicted in FIG. 10, the control had a protein assay absorbance of 0.049; the high power acoustic treatment at atmospheric pressure (15 psi) had an absorbance of 0.174; and the high power acoustic treatment at 45 psi had an absorbance of 0.415. High power acoustic treatment at atmospheric pressure resulted in a 3.5-fold increase in the protein assay absorbance over the control. High power acoustic treatment at elevated pressure, namely 45 psi, resulted in an 8-fold increase in the protein assay absorbance over the control and a 2-fold increase over the high power treatment at atmospheric pressure, and appeared to reach end-point in 12 minutes.

Those skilled in the art will know, or be able to ascertain using no more than routine experimentation, many equivalents to the embodiments and practices described herein. Accordingly, it will be understood that the invention is not to be limited to the illustrative embodiments disclosed herein. Other illustrative devices, systems, methods, applications, and features of the invention are described in the following documents which are hereby incorporated by reference herein:

1. U.S. Pat. No. 6,719,449 entitled "Apparatus and Method for Controlling Sonic Treatment"
2. U.S. application Ser. No. 11/001,988, filed Dec. 2, 2004, and entitled "Apparatus and Methods for Sample Preparation"
3. U.S. Pat. No. 6,948,843 entitled "Method and apparatus for acoustically controlling liquid solutions in microfluidic devices"

The first-named reference above discloses apparatuses and methods for exposing a sample to acoustic energy and for selectively controlling acoustic energy and/or the location of the sample relative to acoustic energy that may be used in conjunction with the invention disclosed herein. In particular, the first reference discloses various acoustic energy sources, electronics and waveforms, positioning systems, sensors, control systems, sample vessels, materials for treatments, and applications of acoustic treatment.

The second-named reference above discloses systems, methods, and devices relating to processing a sample that may be used in conjunction with the invention disclosed herein. In particular, the second reference discloses various sample vessels and systems and methods for collecting, stabilizing, fragmenting and/or analyzing samples.

The third-named reference above discloses systems, methods, and devices relating to coupling acoustic energy to a sample vessel to lower acoustic energy requirements to obtain desired process results, such as mixing.

The subject matter discussed above can readily be adapted for use in the systems and methods disclosed in the above references. It should be noted that Applicants consider all operable combinations of the disclosed illustrative embodiments to be patentable subject matter including combinations of the subject matter disclosed in the above references.

The invention claimed is:

1. A system for applying acoustic energy to a sample, comprising
   a housing;
   a vessel disposed within the housing for containing the sample;
   a chamber disposed within the housing for receiving the vessel;
   an acoustic energy source disposed within the housing, the acoustic energy source providing a focused acoustic field having a frequency of between about 100 kilohertz and about 100 megahertz and a width of less than about 2 cm to the sample contained in the vessel according to a treatment protocol;
   a processor disposed within the housing and in communication with the acoustic energy source, the processor for controlling the treatment protocol;
   at least one sensor in communication with the processor, wherein the at least one sensor detects information about at least one of a viscosity of the sample, presence of a solid in the sample, or a volume of the sample; and
   a user interface for displaying an indication based on the information detected by the at least one sensor of the at least one of the viscosity of the sample, the presence of a solid in the sample, or the volume of the sample, wherein the treatment protocol is adjusted based on a user input provided via the user interface and based at least in part on the at least one of the viscosity of the sample, the presence of a solid in the sample, or the volume of the sample that is detected, and wherein the user interface is configured to present a query that requires user input for adjustment of the treatment protocol in response to a determination that a condition exists in the vessel, the determination being made based on information detected by the at least one sensor, and wherein adjustment of the treatment protocol comprises modification of at least one parameter of treatment provided by the focused acoustic field.

2. The system of claim 1, wherein the at least one sensor comprises at least one of an optical sensor, an infrared sensor, a microscope, a video camera, a laser, and an acoustic sensor.

3. The system of claim 1, further comprising a sample holder for holding the vessel containing the sample, wherein the sample holder is capable of detecting characteristics of the sample.

4. The system of claim 1, wherein the at least one sensor detects identification information of the sample via an identifying mark.

5. The system of claim 4, wherein the identifying mark comprises at least one of a radio frequency identification tag, text, a barcode, a symbol, and a reflective material.

6. The system of claim 1, wherein the processor modifies parameters of the treatment protocol based at least in part on information about the sample detected while the focused acoustic field is applied to the sample.

7. The system of claim 1, comprising a memory in communication with the processor for storing a plurality of treatment protocols, wherein the processor is capable of determining the treatment protocol by selecting one of the plurality of treatment protocols stored in the memory.

8. The system of claim 7, wherein the memory comprises an interchangeable memory component.

9. The system of claim 8, wherein the interchangeable memory component comprises at least one of a memory card, a flash drive, a CD, a DVD, a CD-ROM, a diskette, and a chip.

10. The system of claim 1, wherein the user interface comprises an input mechanism that when activated initiates application of a focused acoustic field provided by the acoustic energy source to the sample.

11. The system of claim 1, comprising a coupling medium disposed within the housing and through which the focused acoustic field is applied to the sample.

12. The system of claim 11, wherein the coupling medium comprises at least one of fluid, water, gel, and rubber.

13. The system of claim 1, wherein the user interface queries the user for input corresponding to a characteristic of the sample.

14. The system of claim 1, wherein the user interface queries the user for input corresponding to a parameter for the treatment protocol.

15. The system of claim 14, wherein the parameter comprises at least one of a pulse shape of a waveform, a duty cycle, an intensity, a frequency, a burst pattern, energy delivered to the sample, a pressure of the chamber, and a distance between the acoustic energy source and the sample.

16. The system of claim 1, wherein the user interface queries the user for input corresponding to an objective of the treatment protocol.

17. The system of claim 16, wherein the objective comprises at least one of sterilization, mixing, reaction enhancement, stirring, solubilization, heating, fluidization, and comminution.

18. The system of claim 1, wherein the sample comprises at least one of food, a cosmetic, and paint.

19. The system of claim 1, wherein the user interface prompts the user for a limitation on at least one of a parameter of the treatment protocol and a characteristic of the sample and the processor determines a treatment protocol according to the limitation.

20. The system of claim 1, wherein the focused acoustic field substantially converges in a focal zone having a diameter less than about 2 centimeters.

21. The system of claim 1, wherein the user interface comprises a display for displaying at least one of characteristics of the sample, parameters of the treatment protocol, available treatment protocols, objective of the treatment protocol, prompts to the user, identification information of the sample, and a state of the sample.

22. The system of claim 1, wherein the user interface alerts the user when the acoustic energy source has finished providing the focused acoustic field to the sample according to the treatment protocol.

23. The system of claim 1, wherein the processor is in communication with at least one of a processor external to the housing and a memory external to the housing.

24. The system of claim 1, comprising a positioning mechanism in communication with the processor for positioning the sample relative to the acoustic energy source.

25. The system of claim 1, wherein the housing is between about 5 centimeters and about 30 centimeters along at least one of width, height, and length.

26. The system of claim 1, comprising an access mechanism on or near the surface of the housing and through which the chamber may be accessed for placement of the sample within the chamber, wherein the access mechanism is capable of being in one of an open state to allow access to the chamber or a closed state to seal the chamber.

27. The system of claim 26, wherein the chamber comprises a sample holder capable of detecting when the sample is disposed within the sample holder and the access mechanism automatically switches to the closed state when the sample holder detects the sample.

28. The system of claim 26, wherein the processor prevents the acoustic energy source from providing acoustic energy when the access mechanism is in the open state.

29. The system of claim 26, wherein the access mechanism automatically switches to the closed state when the user interface receives an input that initiates application of a focused acoustic field provided by the acoustic energy source to the sample.

30. The system of claim 26, comprising a motion detector on the surface of the housing for detecting motion near the housing, wherein the access mechanism automatically switches to the open state when the motion detector detects motion.

31. A system for applying acoustic energy to a sample, comprising
a housing;
a vessel disposed within the housing for containing the sample;
a chamber disposed within the housing for receiving the vessel;
an acoustic energy source disposed within the housing, the acoustic energy source providing a focused acoustic field having a frequency of between about 100 kilohertz and about 100 megahertz and a width of less than about 2 cm to the sample contained in the vessel according to a treatment protocol;
a processor disposed within the housing and in communication with the acoustic energy source, the processor for controlling the treatment protocol;
at least one sensor in communication with the processor, wherein the at least one sensor detects information about at least one of a viscosity of the sample, presence of a solid in the sample, or a volume of the sample; and
a user interface that displays an indication based on the information detected by the at least one sensor of the at least one of the viscosity of the sample, the presence of a solid in the sample, or the volume of the sample, wherein the treatment protocol is automatically adjusted by the processor based at least in part on the at least one of the viscosity of the sample, the presence of a solid in the sample, or the volume of the sample that is detected, and wherein the user interface is configured to present a query that requires user input for adjustment of the treatment protocol in response to a determination that a condition exists in the vessel, the determination being made based on information detected by the at least one sensor, and wherein adjustment of the treatment protocol comprises modification of at least one parameter of treatment provided by the focused acoustic field.

32. The system of claim 1, wherein the at least one sensor detects information about the viscosity of the sample, the user interface displays an indication based on the information about the viscosity of the sample, and the treatment protocol is adjusted based on a user input provided via the user interface based on the viscosity of the sample.

33. The system of claim 31, wherein the at least one sensor detects information about the viscosity of the sample, the user interface displays an indication based on the information about the viscosity of the sample, and the treatment protocol is automatically adjusted by the processor based on the viscosity of the sample.

34. The system of claim 1, further comprising a temperature sensor or a pressure sensor.

* * * * *